United States Patent
Baldwin et al.

(10) Patent No.: US 11,596,516 B2
(45) Date of Patent: Mar. 7, 2023

(54) HEART VALVE REGURGITATION ANCHOR AND DELIVERY TOOL

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: Katherine L. Baldwin, Apple Valley, MN (US); James P. Rohl, Prescott, WI (US); James K. Cawthra, Jr., Ramsey, MN (US); Joseph A. Dearani, Rochester, MN (US); Daniel Shuey, Circle Pines, MN (US); Dale Groth, Forest Lake, MN (US)

(73) Assignees: Boston Scientific Scimed, Inc., Maple Grove, MN (US); Mayo Foundation for Medical Education and Research, Rochester, MN (US)

(*) Notice: Subject to any disclaimer, the term of this patent is extended or adjusted under 35 U.S.C. 154(b) by 340 days.

(21) Appl. No.: 16/902,477

(22) Filed: Jun. 16, 2020

(65) Prior Publication Data

US 2020/0306042 A1 Oct. 1, 2020

Related U.S. Application Data

(63) Continuation of application No. 15/678,327, filed on Aug. 16, 2017, now Pat. No. 10,702,384.

(Continued)

(51) Int. Cl.
*A61F 2/24* (2006.01)
*A61B 17/122* (2006.01)
(Continued)

(52) U.S. Cl.
CPC ........ *A61F 2/2442* (2013.01); *A61B 17/0401* (2013.01); *A61B 17/06* (2013.01);
(Continued)

(58) Field of Classification Search
CPC ........ A61F 2/24; A61F 2/2442; A61F 2/2427; A61F 2/2418; A61F 2/2412;
(Continued)

(56) References Cited

U.S. PATENT DOCUMENTS

| 5,634,936 A | 6/1997 | Linden et al. |
| 5,853,422 A | 12/1998 | Huebsch et al. |

(Continued)

FOREIGN PATENT DOCUMENTS

| WO | 2006039199 A2 | 4/2006 |
| WO | 2007009021 A2 | 1/2007 |
| WO | 2007070753 A2 | 6/2007 |

OTHER PUBLICATIONS

International Search Report and Written Opinion dated Nov. 29, 2017 for International Application No. PCT/US2017/047073.

*Primary Examiner* — Vi X Nguyen
(74) *Attorney, Agent, or Firm* — Seager, Tufte & Wickhem LLP

(57) ABSTRACT

A heart valve anchor apparatus may include a body having a proximal portion and a distal portion. The body may include a first radially expandable portion at the proximal portion of the body, a second radially expandable portion at the distal portion of the body, and a root portion extending from the first radially expandable portion to the second radially expandable portion, the root portion having an outer extent. The first radially expandable portion may be configured to self-expand to an outer extent greater than the outer extent of the root portion when radially unconstrained. The second radially expandable portion may be configured to (Continued)

self-expand to an outer extent greater than the outer extent of the root portion when radially unconstrained. In an unstressed configuration, the body may define a longitudinal centerline that extends away from a plane tangent to the root portion.

2 Claims, 46 Drawing Sheets

Related U.S. Application Data

(60) Provisional application No. 62/375,564, filed on Aug. 16, 2016.

(51) Int. Cl.
*A61B 17/06* (2006.01)
*A61B 17/062* (2006.01)
*A61B 17/04* (2006.01)
*A61B 17/00* (2006.01)
*A61B 17/128* (2006.01)
*A61B 90/00* (2016.01)

(52) U.S. Cl.
CPC ........ *A61B 17/062* (2013.01); *A61B 17/1227* (2013.01); *A61F 2/2466* (2013.01); *A61B 17/06066* (2013.01); *A61B 17/128* (2013.01); *A61B 2017/00243* (2013.01); *A61B 2017/00336* (2013.01); *A61B 2017/00783* (2013.01); *A61B 2017/00867* (2013.01); *A61B 2017/0404* (2013.01); *A61B 2017/0409* (2013.01); *A61B 2017/0414* (2013.01); *A61B 2017/0417* (2013.01); *A61B 2017/0419* (2013.01); *A61B 2017/0464* (2013.01); *A61B 2017/0608* (2013.01); *A61B 2017/06052* (2013.01); *A61B 2090/3966* (2016.02); *A61F 2210/0014* (2013.01); *A61F 2220/0075* (2013.01); *A61F 2230/0006* (2013.01)

(58) Field of Classification Search
CPC ...... A61F 2/2466; A61F 2/2436; A61B 17/04; A61B 17/12; A61B 17/122; A61B 17/0401; A61B 17/06
See application file for complete search history.

(56) References Cited

U.S. PATENT DOCUMENTS

| | | | |
|---|---|---|---|
| 6,024,756 | A | 2/2000 | Huebsch et al. |
| 6,029,806 | A * | 2/2000 | Cerwin ............ A61B 17/06138 53/118 |
| 6,117,159 | A | 9/2000 | Huebsch et al. |
| 6,270,515 | B1 | 8/2001 | Linden et al. |
| 6,312,446 | B1 | 11/2001 | Huebsch et al. |
| 8,357,193 | B2 | 1/2013 | Phan et al. |
| 8,454,632 | B2 | 6/2013 | Binmoeller et al. |
| 8,961,594 | B2 | 2/2015 | Maisano et al. |
| 8,961,596 | B2 | 2/2015 | Maisano et al. |
| 9,241,702 | B2 | 1/2016 | Maisano et al. |
| 2003/0199974 | A1 | 10/2003 | Lee et al. |
| 2005/0250986 | A1 | 11/2005 | Rothe et al. |
| 2005/0250988 | A1 | 11/2005 | Ewers et al. |
| 2007/0073337 | A1 | 3/2007 | Abbott et al. |
| 2012/0296349 | A1 | 11/2012 | Smith et al. |
| 2015/0045879 | A1 * | 2/2015 | Longoria ............ A61B 17/0401 623/2.12 |

* cited by examiner

HEART VALVE REGURGITATION ANCHOR AND DELIVERY TOOL

CROSS REFERENCE TO RELATED APPLICATIONS

The present application claims priority to U.S. application Ser. No. 15/678,327, filed Aug. 16, 2017 which claims benefit of and priority to U.S. Provisional Patent Application Ser. No. 62/375,564, filed Aug. 16, 2016, the disclosures of which are incorporated herein by reference

TECHNICAL FIELD

The present disclosure pertains to medical devices, and methods for manufacturing and/or using medical devices. More particularly, the present disclosure pertains to configurations of heart valve regurgitation anchors and delivery tools for heart valve regurgitation anchors.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and/or using medical devices.

SUMMARY

In a first aspect, a heart valve anchor apparatus may comprise a body having a proximal portion, a proximal end, a distal portion, and a distal end, the body having a delivery configuration, an unstressed configuration, and a shortened configuration. The body may comprise a first radially expandable portion at the proximal portion of the body, a second radially expandable portion at the distal portion of the body, and a root portion extending from the first radially expandable portion to the second radially expandable portion, the root portion having an outer extent. The first radially expandable portion may be configured to self-expand to an outer extent greater than the outer extent of the root portion when radially unconstrained. The second radially expandable portion may be configured to self-expand to an outer extent greater than the outer extent of the root portion when radially unconstrained. In the unstressed configuration, the body may define a longitudinal centerline that extends away from a plane tangent to the root portion.

In addition or alternatively, and in a second aspect, the body is adapted to be housed at least partially within a tissue penetrating device in the delivery configuration.

In addition or alternatively, and in a third aspect, the body is adapted to engage tissue between the proximal portion and the distal portion in the unstressed configuration and the shortened configuration, such that one or more plications of tissue are formed between the proximal portion and the distal portion.

In addition or alternatively, and in a fourth aspect, the body is adapted to compress tissue between the proximal portion and the distal portion in the shortened configuration.

In addition or alternatively, and in a fifth aspect, the root portion is adapted to pass through tissue disposed between the proximal portion and the distal portion.

In addition or alternatively, and in a sixth aspect, the body has an overall length in the unstressed configuration and the overall length is reduced when the body is in the shortened configuration.

In addition or alternatively, and in a seventh aspect, the heart valve anchor apparatus may further comprise a suture element disposed through the body along the longitudinal centerline.

In addition or alternatively, and in an eighth aspect, the heart valve anchor apparatus may further comprise a needle, a suture element having a proximal end attached to the needle, and an elongated sheath having a deployment head fixedly attached at a proximal end of the elongated sheath. The suture element may pass distally into the deployment head and have a stop feature disposed within the deployment head. The body may be disposed at least partially within the elongated sheath.

In addition or alternatively, and in a ninth aspect, translation of the elongated sheath proximally relative to the body releases the body such that the body is free to assume the unstressed configuration.

In addition or alternatively, and in a tenth aspect, in the delivery configuration, the first radially expandable portion is disposed within the elongated sheath and the second radially expandable portion is disposed distal of the elongated sheath.

In addition or alternatively, and in an eleventh aspect, the stop feature is disposed proximal of the first radially expandable portion.

In addition or alternatively, and in a twelfth aspect, the heart valve anchor apparatus may further comprise a tissue penetrating device including a lumen extending longitudinally therethrough, the body being disposed within the lumen in the delivery configuration, and a push rod disposed within the lumen adjacent to the body. Translation of the push rod relative to the tissue penetrating device may release the body from the lumen. After release from the lumen, the body may assume the unstressed configuration.

In addition or alternatively, and in a thirteenth aspect, the heart valve anchor further includes a suture element extending longitudinally through the body to a stop feature disposed opposite the push rod, wherein placing the suture element in tension while applying an opposing force to the body with the push rod places the body into a shortened configuration wherein the tissue is compressed between the first radially expandable portion and the second radially expandable portion.

In addition or alternatively, and in a fourteenth aspect, a method of deploying a heart valve anchor apparatus may comprise:

inserting a tissue penetrating device into tissue forming a heart valve annulus such that a distal end of the tissue penetrating device protrudes from the tissue, the tissue penetrating device having a heart valve anchor apparatus disposed within a lumen of the tissue penetrating device in a delivery configuration, the heart valve anchor apparatus comprising a body comprising a first radially expandable portion at a proximal portion of the body, a second radially expandable portion at a distal portion of the body, and a root portion extending from the first radially expandable portion to the second radially expandable portion, the root portion having an outer extent, wherein the first radially expandable portion is configured to self-expand to an outer extent greater than the outer extent of the root portion when radially unconstrained, wherein the second radially expandable portion is configured to self-expand to an outer extent greater than the outer extent of the root portion when radially unconstrained;

actuating a handle element of the tissue penetrating device to push the second radially expandable portion out of the distal end of the tissue penetrating device outside of the tissue; and withdrawing the tissue penetrating device through the tissue, thereby releasing the root portion within the tissue and the first radially expandable portion outside of the tissue, such that the first radially expandable portion and the second radially expandable portion both engage the tissue disposed between them in an unstressed configuration;

wherein in the unstressed configuration, the body defines a longitudinal centerline that extends away from a plane tangent to the root portion.

In addition or alternatively, and in a fifteenth aspect, the heart valve anchor apparatus further includes a suture element extending longitudinally through the body to a stop feature disposed distally of the second radially expandable portion, and the method further includes the step of applying tension to a proximal portion of the suture element while applying a distally-directed force to the proximal portion of the body to place the body into a shortened configuration wherein the tissue is compressed between the first radially expandable portion and the second radially expandable portion.

In addition or alternatively, and in a sixteenth aspect, a method of deploying a heart valve anchor apparatus may comprise:

inserting a tissue penetrating device into tissue forming a heart valve annulus such that a proximal end of the tissue penetrating device protrudes from the tissue, the tissue penetrating device having a proximal end of a suture element attached to a distal portion of the tissue penetrating device, the suture element of the tissue penetrating device passing into a deployment head fixedly attached at a proximal end of an elongated sheath, wherein at least a portion of a heart valve anchor apparatus is disposed within a lumen of the elongated sheath in a delivery configuration, the heart valve anchor apparatus comprising a body comprising a first radially expandable portion at a proximal portion of the body, a second radially expandable portion at a distal portion of the body, and a root portion extending from the first radially expandable portion to the second radially expandable portion, the root portion having an outer extent, wherein the first radially expandable portion is configured to self-expand to an outer extent greater than the outer extent of the root portion when radially unconstrained, wherein the second radially expandable portion is configured to self-expand to an outer extent greater than the outer extent of the root portion when radially unconstrained, wherein in the delivery configuration, the first radially expandable portion is disposed within the elongated sheath and the second radially expandable portion is disposed distally of the elongated sheath;

pulling the tissue penetrating device away from the tissue such that the deployment head passes through the tissue and the second radially expandable portion is engaged against the tissue; and pulling the elongated sheath away from the second radially expandable portion, thereby releasing the root portion within the tissue and the first radially expandable portion outside of the tissue, such that the first radially expandable portion and the second radially expandable portion both engage the tissue disposed between them in an unstressed configuration;

wherein in the unstressed configuration, the body defines a longitudinal centerline that extends away from a plane tangent to the root portion.

In addition or alternatively, and in a seventeenth aspect, the suture element includes a stop feature disposed within the deployment head. After engaging the second radially expandable portion against the tissue, further pulling the tissue penetrating device away from the tissue engages the stop feature with a proximal end of the deployment head to pull the elongated sheath away from the second radially expandable portion.

In addition or alternatively, and in an eighteenth aspect, the heart valve anchor includes a suture element extending distally from the second radially expandable portion, and the method further includes the step of applying tension to a distal portion of the suture element of the heart valve anchor while applying a proximally-directed force to the distal portion of the body to place the body into a shortened configuration wherein the tissue is compressed between the first radially expandable portion and the second radially expandable portion.

In addition or alternatively, and in a nineteenth aspect, the suture element of the tissue penetrating device passes through elongated sheath and the body, and includes a stop feature disposed within the deployment head. Pulling the elongated sheath away from the second radially expandable portion includes grasping the deployment head with a tool and pulling the elongated sheath away from the second radially expandable portion along and relative to the suture element.

In addition or alternatively, and in a twentieth aspect, a method of deploying a heart valve anchor apparatus may further comprise severing the suture element of the tissue penetrating device proximal of the stop feature, and applying tension to a portion of the suture element of the tissue penetrating device distal to the second radially expandable portion while applying a proximally-directed force to the distal portion of the body to place the body into a shortened configuration wherein the tissue is compressed between the first radially expandable portion and the second radially expandable portion.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
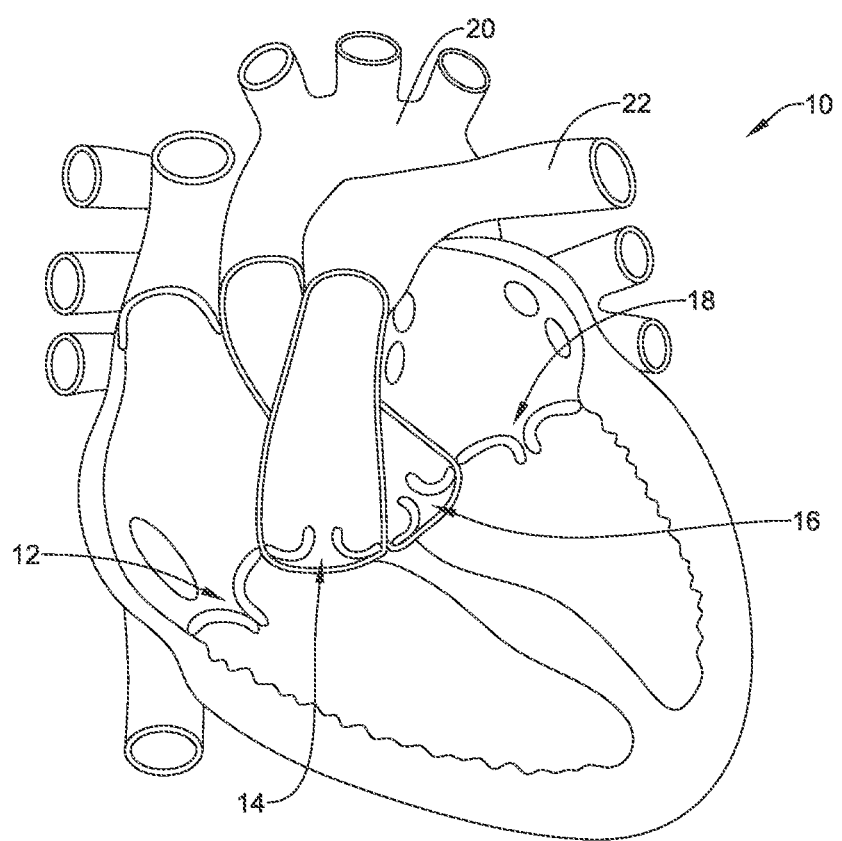
FIG. 1 is a partial cut-away view of an example heart.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Some mammalian hearts (e.g., human, etc.) include four heart valves: a tricuspid valve 12, a pulmonary valve 14, an aortic valve 16, and a mitral valve 18, as seen in an example heart 10 illustrated in FIG. 1. The purpose of the heart valves is to allow blood to flow through the heart 10 and from the heart 10 into the major blood vessels connected to the heart 10, such as the aorta 20 and the pulmonary artery 22, for example. In a normally functioning heart valve, blood is permitted to pass or flow downstream through the heart valve (e.g., from an atrium to a ventricle, from a ventricle to an artery, etc.) when the heart valve is open, and when the heart valve is closed, blood is prevented from passing or flowing back upstream through the heart valve (e.g., from a ventricle to an atrium, etc.). When regurgitation occurs, a heart valve fails to open and/or close properly such that blood is permitted to pass or flow back upstream through the heart valve (e.g., from a ventricle to an atrium, etc.). In some cases, the defective heart valve may have leaflets that may not close, or may not be capable of closing, completely. One possible remedy is an annular reduction procedure that may be performed to reduce an overall extent of the defective heart valve to bring the heart valve leaflets closer together, thereby permitting the heart valve leaflets to properly close the heart valve to the passage of blood.

Disclosed herein are apparatus, medical devices, and/or methods that may be used to diagnose, treat, and/or repair a portion of the cardiovascular system. At least some of the apparatus, medical devices, and/or methods disclosed herein may include and/or be used to deliver and implant a heart valve anchor. In addition, the apparatus and/or medical devices disclosed herein may deliver a heart valve anchor using open-heart surgical methods or via minimally-invasive intravascular techniques. The devices and methods disclosed herein may also provide a number of additional desirable features and/or benefits as described in more detail below.

Figure 2:
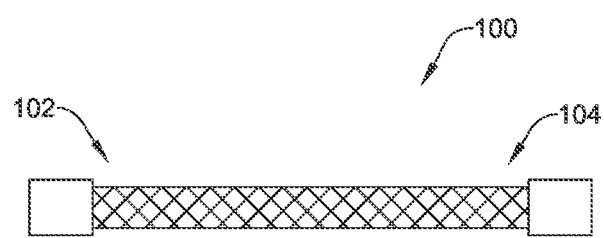
FIGS. 2-12 illustrate example bodies associated with a heart valve anchor apparatus.
Figure 3:
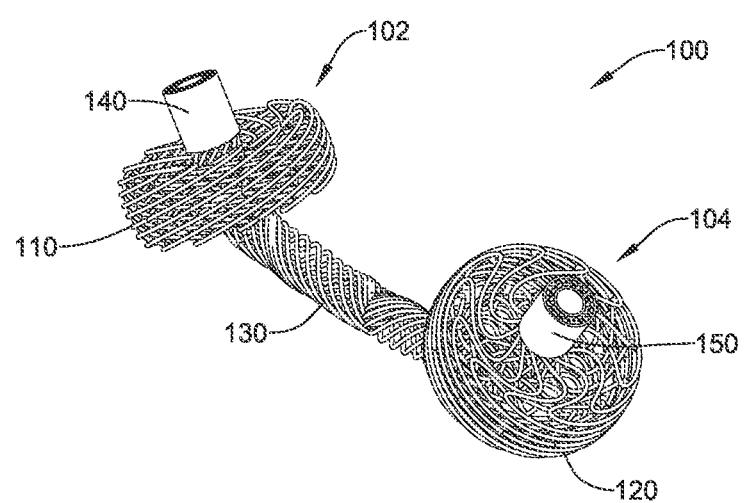
Figure 4:
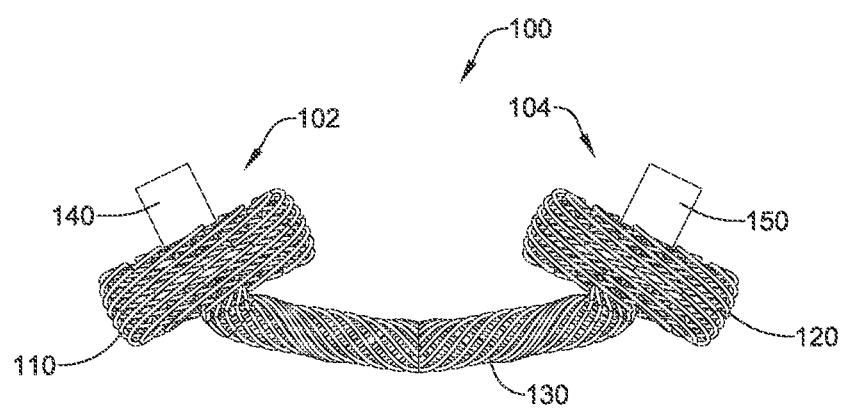

An example heart valve anchor apparatus may include a body 100 configured and/or adapted to transition between a collapsed or delivery configuration, as illustrated in FIG. 2, and an expanded or unstressed configuration, as illustrated in FIGS. 3 and 4. In some embodiments, the body 100 may be further configured and/or adapted to transition between the unstressed configuration and a shortened configuration, as will be described further below. Other embodiments, aspects, and/or examples may be described herein, wherein like reference numerals (e.g., 100, 200, 300, etc.) refer to similar elements among the various embodiments, aspects, and/or examples. In some embodiments, the body 100 may have a proximal portion 102 proximate a proximal end, and a distal portion 104 proximate a distal end.

In some embodiments, the body 100 may comprise a first radially expandable portion 110 at the proximal portion 102 of the body 100, a second radially expandable portion 120 at the distal portion 104 of the body 100, and a root portion 130 extending from the first radially expandable portion 110 to the second radially expandable portion 120. In some embodiments, the first radially expandable portion 110 and/or the second radially expandable portion 120 may extend radially outward from the root portion 130 in the expanded or unstressed configuration. In some embodiments, the first radially expandable portion 110 and/or the second radially expandable portion 120 may form a bulbous shape, a disc-like shape, a concave shape, a convex shape, and/or combinations of these shapes in the expanded or unstressed configuration.

The body 100 may include a stent structure and/or be formed from a plurality of wires. In some embodiments, the plurality of wires may be oriented and/or formed into a braided configuration. In some embodiments, the body 100, including the first radially expandable portion 110, the second radially expandable portion 120, and the root portion 130 may be unitarily formed. In other words, each of the plurality of wires may extend from the proximal end to the distal end and form a portion of each of the first radially expandable portion 110, the second radially expandable portion 120, and the root portion 130. Other arrangements and configurations are also contemplated. In some embodiments, the plurality of wires may include about 4 wires to about 50 wires (e.g., 4, 6, 8, 10, 12, 16, 18, 24, 32 wires, etc.). In some embodiments, the plurality of wires may include wires having a size (e.g., diameter, etc.) of about 0.0127 mm (0.0005 inches) to about 0.127 mm (0.005 inches). In some embodiments, the plurality of wires may be metallic wires, polymeric wires, composite wires, and/or other biocompatible materials. Some suitable non-limiting materials for the plurality of wires are described below.

In some embodiments, the body 100 may be tubular and/or may include a lumen extending between the proximal end and the distal end of the body 100 through the proximal portion 102, the first radially expandable portion 110, the root portion 130, the distal portion 104, and/or the second radially expandable portion 120. In some embodiments, the body 100 may include a proximal coupler 140 extending from the first radially expandable portion 110 toward and/or to the proximal end. In some embodiments, the body 100 may include a distal coupler 150 extending from the second radially expandable portion 120 toward and/or to the distal end. In some embodiments, the proximal coupler 140 and/or the distal coupler 150 may each be a tubular structure disposed about at least a part of the proximal portion 102 and/or the distal portion 104, respectively. In some embodiments, the proximal coupler 140 and/or the distal coupler 150 may each be configured to bind the plurality of wires together to prevent the stent structure and/or the braided configuration from becoming unraveled. In some embodiments, the proximal coupler 140 and/or the distal coupler 150 may be fixedly attached (e.g., welded, crimped, etc.) to the proximal end and/or the distal end, respectively, of the body 100. In some embodiments, the body 100 may include an inner tubular member disposed within and/or fixedly attached to the plurality of wires at and/or adjacent to each of the proximal end and the distal end.

In some embodiments, the root portion 130 may be configured to expand or self-expand radially outward between the collapsed or delivery configuration and the expanded or unstressed configuration. In some embodiments, the root portion 130 may have and/or define a maximum outer extent, measured radially or in cross-section for example, in the expanded or unstressed configuration. In some embodiments, the root portion 130 may have a length, or a longitudinal distance between the first radially expandable portion 110 and the second radially expandable portion 120, of about 3 mm to about 30 mm (e.g., 3, 5, 7, 10, 12, 15, 20, 25, 30 mm, etc.). In some embodiments, the maximum outer extent and/or diameter of the root portion 130 may be from about 0.250 mm to about 30 mm (e.g., 0.250, 0.5, 0.75, 1, 2, 3, 5, 7, 10, 13, 15, 20, 30 mm, etc.).

In some embodiments, the first radially expandable portion 110 may be configured to be expanded and/or to self-expand to an outer extent greater than the maximum outer extent of the root portion 130 when radially unconstrained (e.g., when in the unstressed configuration, the shortened configuration, when not in the delivery configuration, etc.). In some embodiments, the second radially expandable portion 120 may be configured to be expanded and/or to self-expand to an outer extent greater than the maximum outer extent of the root portion 130 when radially unconstrained (e.g., when in the unstressed configuration). In at least some embodiments, the first radially expandable portion 110 and the second radially expandable portion 120 may include and/or be formed having a similar or the same outer extent, size, and/or shape. For example, in some embodiments, the first radially expandable portion 110 and/or the second radially expandable portion 120 may have a generally round outer shape or profile defining an outer diameter. In some embodiments, the first radially expandable portion 110 and the second radially expandable portion 120 may have a maximum outer diameter or outer extent of about 2 mm to about 30 mm (e.g., 2, 3, 4, 5, 7, 10, 15, 20, 30 mm, etc.). A maximum length of the first radially expandable portion 110 and/or the second radially expandable portion 120 along a central or longitudinal axis or centerline of the body 100 may be from about 0.5 mm to about 15 mm (e.g., 0.5, 1, 2, 4, 5, 7, 8, 10, 15 mm, etc.). Other configurations are also contemplated.

In some embodiments, the body 100 may include and/or define a longitudinal centerline extending between the proximal end and the distal end of the body 100. In some embodiments, the longitudinal centerline may be coincident with and/or coaxial with the lumen extending between the proximal end and the distal end of the body 100. In some embodiments, the longitudinal centerline may not necessarily be an axis or a straight line. As shown in FIG. 4, the root portion 130 may include and/or be formed with at least one curve, arc, bend, angle, and/or other non-straight feature along its length. In some embodiments, the at least one curve, arc, bend, angle, and/or other non-straight feature may extend for the length of the root portion 130. In some embodiments, when the body 100 is in the expanded or unstressed configuration, the longitudinal centerline may extend away from a plane tangent to the root portion 130. In other words, both opposing ends of the longitudinal centerline may extend away from and/or be non-intersecting with the plane tangent to the root portion 130. In some embodiments, the body 100 may have an overall longitudinal length in the compressed or delivery configuration of about 20 mm to about 80 mm (e.g., 20, 25, 30, 40, 50, 60, 75, 80 mm, etc.). In some embodiments, the body 100 may have an overall longitudinal length in the expanded or unstressed configuration of about 10 mm to about 60 mm (e.g., 10, 15, 20, 25, 30, 40, 50, 60 mm, etc.).

In the expanded or unstressed configuration, the first radially expandable portion 110 and/or the second radially expandable portion 120 may extend radially outward from the root portion 130. In some embodiments, the first radially expandable portion 110 and/or the second radially expandable portion 120, and/or a plane through the greatest outer extent of the first and/or second radially expandable portions 110, 120, may be arranged at a non-zero angle relative to the longitudinal centerline. In some embodiments, the first radially expandable portion 110 and/or the second radially expandable portion 120 may be substantially perpendicular to the longitudinal centerline. In some embodiments, the first radially expandable portion 110 and/or the second radially expandable portion 120 may be arranged at an oblique angle to the longitudinal centerline.

Figure 5:
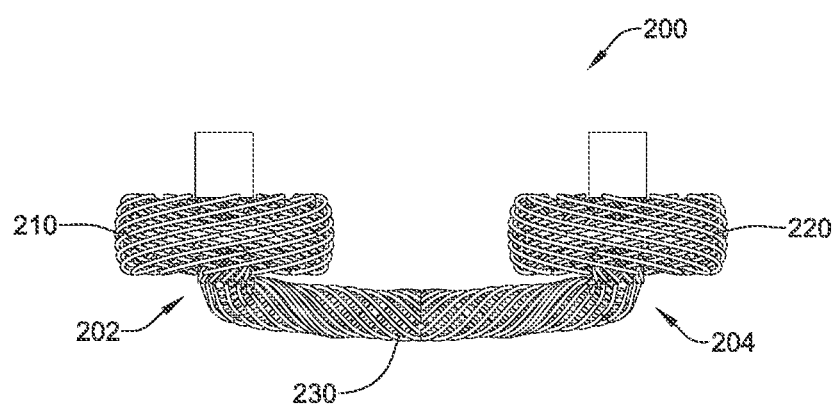
Figure 6:
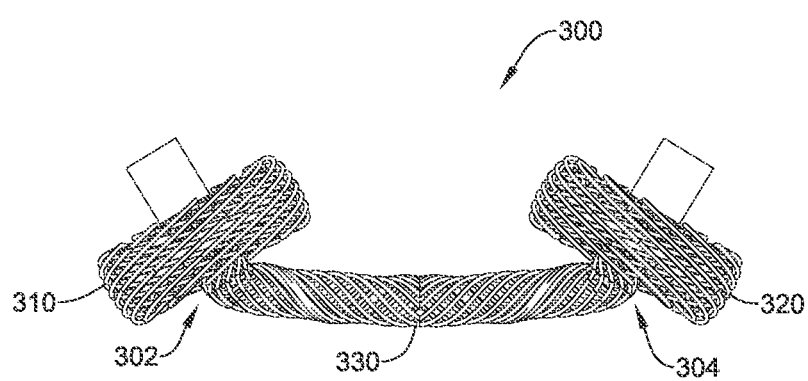

In some embodiments, a body 200, 300 may include a generally straight root portion 230, 330, wherein a proximal portion 202, 302 and a distal portion 204, 304 are arranged at a non-zero angle relative to the root portion 230, 330, as seen in FIGS. 5 and 6, respectively, for example. The bodies 200, 300 may have and/or include similar characteristics and/or features to the body 100, which will not all be repeated in detail in the interest of brevity. In FIG. 5, the proximal portion 202 and the distal portion 204 are arranged to form a bend or curve of approximately 90 degrees relative to the root portion 230. In this case, a first radially expandable portion 210 and a second radially expandable portion 220 may be arranged and/or oriented substantially perpendicular to a longitudinal centerline of the body 200 proximal and distal of the bend or curve, respectively. Other angles and/or arrangements for the first radially expandable portion 210 and the second radially expandable portion 220 are also possible. As seen in FIG. 5, the first radially expandable portion 210 and the second radially expandable portion 220 may be substantially parallel to the root portion 230. The first radially expandable portion 210 and the second radially expandable portion 220 may include and/or be formed having a similar or the same outer extent, size, and/or shape.

In FIG. 6, the proximal portion 302 and the distal portion 304 are arranged to form an oblique bend or curve relative to the root portion 330. In some embodiments, the oblique bend or curve may be between 0 degrees and 90 degrees, between 20 degrees and 70 degrees, or between 30 degrees and 60 degrees relative to the root portion 330. In this case, a first radially expandable portion 310 and a second radially expandable portion 320 may be arranged and/or oriented substantially perpendicular to a longitudinal centerline of the body 300 proximal and distal of the bend or curve, respectively. Other angles and/or arrangements for the first radially expandable portion 310 and the second radially expandable portion 320 are also possible. As seen in FIG. 6, the first radially expandable portion 310 and the second radially expandable portion 320 may be arranged at an oblique angle to the root portion 330. The first radially expandable portion 310 and the second radially expandable portion 320 may include and/or be formed having a similar or the same outer extent, size, and/or shape.

Figure 7:
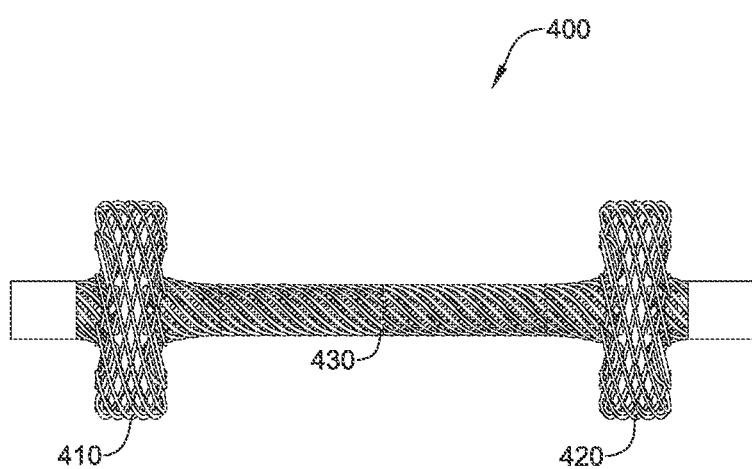

FIG. 7 illustrates a body 400 having characteristics similar to those of the bodies 100-300 which will not all be repeated in detail. As may be seen in FIG. 7, the body 400 may include a first radially expandable portion 410 and a second radially expandable portion 420 having a substantially straight root portion 430 extending between the first radially expandable portion 410 and the second radially expandable portion 420. In FIG. 7, the first radially expandable portion 410 and the second radially expandable portion 420 are arranged substantially perpendicular to the root portion 430 and/or a longitudinal centerline of the body 400. Other angles and/or arrangements for the first radially expandable portion 410 and the second radially expandable portion 420 are also possible. As seen in FIG. 7, the first radially expandable portion 410 and the second radially expandable portion 420 may include and/or be formed having a similar and/or the same outer extent, size, and/or shape, although other configurations are also possible.

Figure 8:
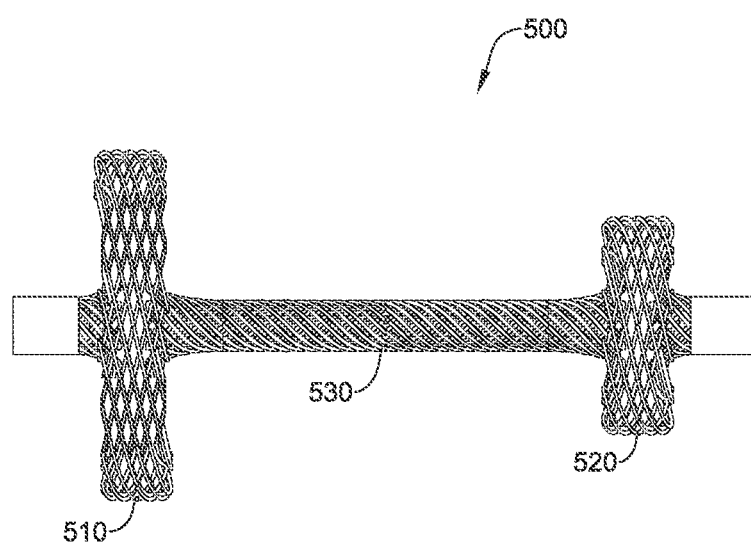

FIG. 8 illustrates a body 500 having characteristics similar to those of the bodies 100-400 which will not all be repeated in detail. As may be seen in FIG. 8, the body 500 may include a first radially expandable portion 510 and a second radially expandable portion 520 having a root portion 530 extending between the first radially expandable portion 510 and the second radially expandable portion 520. In FIG. 8, the first radially expandable portion 510 and the second radially expandable portion 520 are arranged substantially perpendicular to the root portion 530 and/or a longitudinal centerline of the body 500. Other angles and/or arrangements for the first radially expandable portion 510 and the second radially expandable portion 520 are also possible. As seen in FIG. 8, the first radially expandable portion 510 and the second radially expandable portion 520 may include and/or be formed having a different outer extent, size, and/or shape from each other, although other configurations are also possible.

Figure 9:
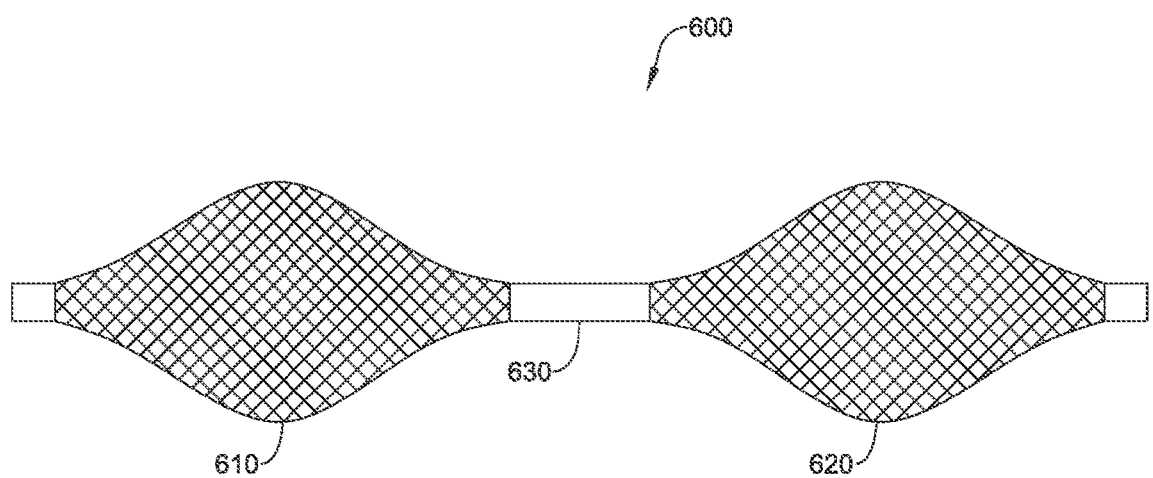

FIG. 9 illustrates a body 600 having characteristics similar to those of the bodies 100-500 which will not all be repeated in detail. As may be seen in FIG. 9, the body 600 may include a first radially expandable portion 610 and a second radially expandable portion 620 having a root portion 630 extending between the first radially expandable portion 610 and the second radially expandable portion 620. In FIG. 9, the first radially expandable portion 610 and the second radially expandable portion 620 have a generally bulbous shape extending radially outward from the root portion 630 and are arranged with a maximum outer extent substantially perpendicular to the root portion 630 and/or a longitudinal centerline of the body 600. Other angles and/or arrangements for the first radially expandable portion 610 and the second radially expandable portion 620 are also possible. In some embodiments, the root portion 630 may include a tubular member disposed over the root portion 630 and/or the root portion 630 may be formed from a tubular member. As seen in FIG. 9, the first radially expandable portion 610 and the second radially expandable portion 620 may include and/or be formed having a similar or the same outer extent, size, and/or shape, although other configurations are also possible.

Figure 10:
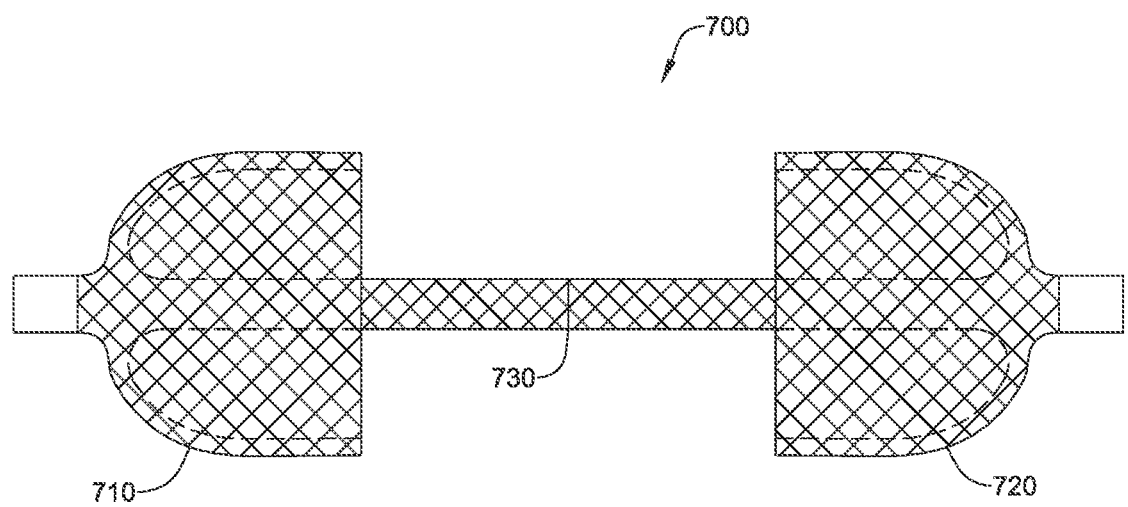

FIG. 10 illustrates a body 700 having characteristics similar to those of the bodies 100-600 which will not all be repeated in detail. As may be seen in FIG. 10, the body 700 may include a first radially expandable portion 710 and a second radially expandable portion 720 having a root portion 730 extending between the first radially expandable portion 710 and the second radially expandable portion 720. In FIG. 10, the first radially expandable portion 710 and/or the second radially expandable portion 720 have a generally convex shape extending radially outward from the root portion 730, as viewed from the proximal end and/or the distal end of the body 700, respectively, and are arranged with a maximum outer extent substantially perpendicular to the root portion 730 and/or a longitudinal centerline of the body 700. In other words, the first radially expandable portion 710 and the second radially expandable portion 720 may extend away from the root portion 730 and toward a longitudinal center of the body 700, as viewed from the side of the body 700. Other angles and/or arrangements for the first radially expandable portion 710 and the second radially expandable portion 720 are also possible. As seen in FIG. 10, the first radially expandable portion 710 and the second radially expandable portion 720 may include and/or be formed having a similar or the same outer extent, size, and/or shape, although other configurations are also possible.

Figure 11:
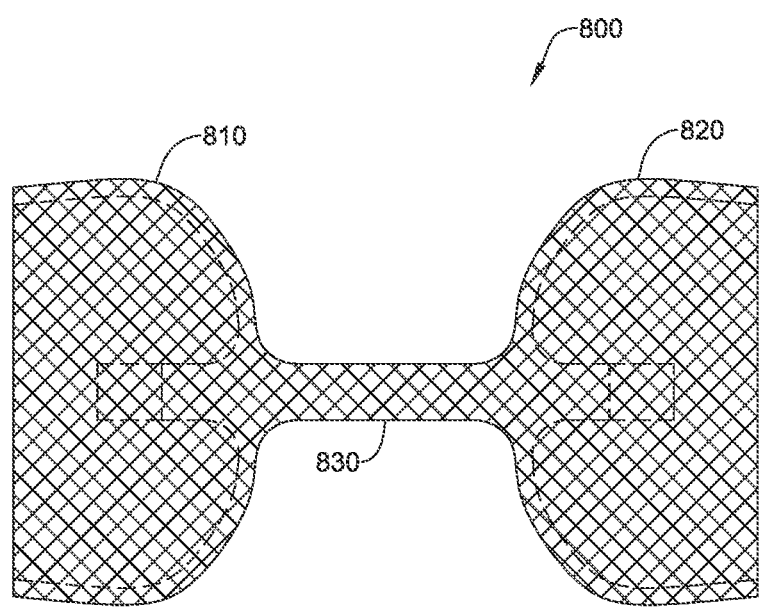

FIG. 11 illustrates a body 800 having characteristics similar to those of the bodies 100-700 which will not all be repeated in detail. As may be seen in FIG. 11, the body 800 may include a first radially expandable portion 810 and a second radially expandable portion 820 having a root portion 830 extending between the first radially expandable portion 810 and the second radially expandable portion 820. In FIG. 11, the first radially expandable portion 810 and/or the second radially expandable portion 820 have a generally concave shape extending radially outward from the root portion 830, as viewed from the proximal end and/or the distal end of the body 800, respectively, and are arranged with a maximum outer extent substantially perpendicular to the root portion 830 and/or a longitudinal centerline of the body 800. In other words, the first radially expandable portion 810 and the second radially expandable portion 820 may extend away from the root portion 830 and toward the proximal end and the distal end of the body 800, respectively, as viewed from the side of the body 800. Other angles and/or arrangements for the first radially expandable portion 810 and the second radially expandable portion 820 are also possible. As seen in FIG. 11, the first radially expandable portion 810 and the second radially expandable portion 820 may include and/or be formed having a similar or the same outer extent, size, and/or shape, although other configurations are also possible.

Figure 12:
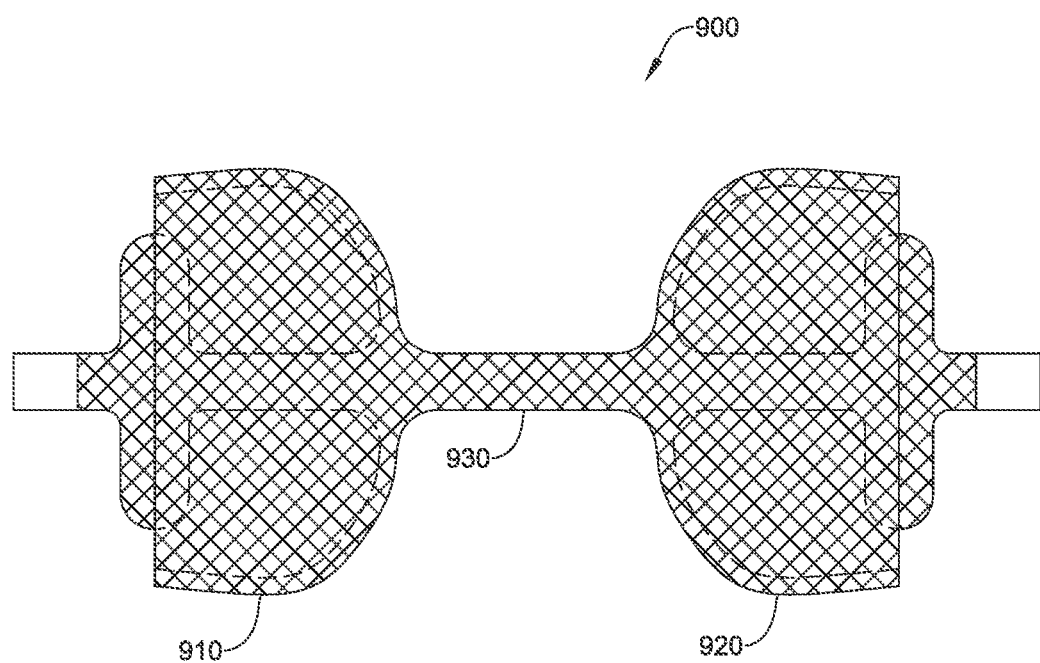

FIG. 12 illustrates a body 900 having characteristics similar to those of the bodies 100-800 which will not all be repeated in detail. As may be seen in FIG. 12, the body 900 may include a first radially expandable portion 910 and a second radially expandable portion 920 having a root portion 930 extending between the first radially expandable portion 910 and the second radially expandable portion 920. In FIG. 12, the first radially expandable portion 910 and/or the second radially expandable portion 920 have a generally concave shape extending radially outward from the root portion 930, as viewed from the proximal end and/or the distal end of the body 900, respectively, and an secondary expandable portion disposed on each of the proximal portion and the distal portion of the body 900. The secondary expandable portion may be positioned within the concave shape of the first radially expandable portion 910 and the second radially expandable portion 920, and/or between the first radially expandable portion 910 and the second radially expandable portion 920 and the proximal end and the distal end, respectively. The first radially expandable portion 910 and the second radially expandable portion 920 are arranged with a maximum outer extent substantially perpendicular to the root portion 930 and/or a longitudinal centerline of the body 900. In other words, the first radially expandable portion 910 and the second radially expandable portion 920 may extend away from the root portion 930 and toward the proximal end and the distal end of the body 900, respectively, as viewed from the side of the body 900. Other angles and/or arrangements for the first radially expandable portion 910 and the second radially expandable portion 920 are also possible. As seen in FIG. 12, the first radially expandable portion 910 and the second radially expandable portion 920 may include and/or be formed having a similar or the same outer extent, size, and/or shape, although other configurations are also possible.

As discussed above, FIGS. 2-12 illustrate some aspects of various possible configurations of a body of a heart valve anchor apparatus. It should be noted that while not explicitly discussed or illustrated, the skilled artisan, in possession of the current disclosure, could easily combine different aspects and/or features of the various configurations discussed above. Combinations of shapes, sizes, angles, orientations, and/or other defining characteristics of the disclosed bodies or elements thereof are fully contemplated within the scope of this disclosure. In order to facilitate understanding, the following discussion may be directed toward the body 100, but it is to be understood that any of the above disclosed bodies and/or combinations of elements thereof may be used in place of the body 100 below with no modification(s) or minor modification(s) within the capabilities of the skilled person.

Figure 13:
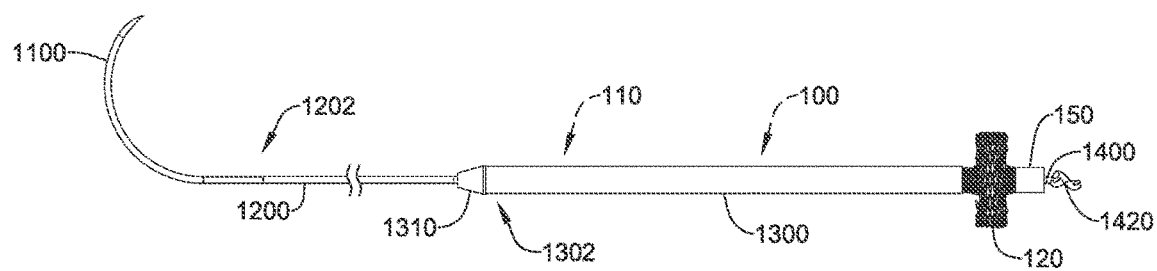
FIGS. 13-13A illustrate an example heart valve anchor apparatus.
Figure 13A:
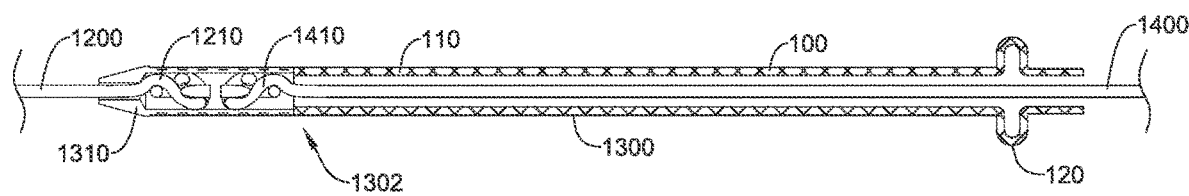

FIGS. 13 and 13A illustrate an example heart valve anchor apparatus including the body 100 housed at least partially within an example tissue penetrating device, such as an elongated sheath 1300, in a delivery configuration. In some embodiments, the heart valve anchor apparatus may include a needle 1100, a suture element 1200 having a proximal end 1202 attached to the needle 1100, and an elongated sheath 1300 having a deployment head 1310 fixedly attached at a proximal end 1302 of the elongated sheath 1300. The elongated sheath 1300 and/or the deployment head 1310 may include a lumen extending therethrough. The suture element 1200 may pass distally into the lumen of the deployment head 1310 and may have or include a stop feature 1210 disposed within the deployment head 1310. The body 100 may be at least partially disposed within the lumen of the elongated sheath 1300 and/or a portion of the body 100 may extend distally from the lumen of the elongated sheath 1300. The body 100 may have a second suture element 1400 extending through the lumen of the body 100 along the longitudinal centerline. The second suture element 1400 may be separate from and/or independent of the suture element 1200. In some embodiments, the second suture element 1400 may include a first stop feature 1410 disposed proximally of the body 100 within the elongated sheath 1300 and/or the deployment head 1310, and a second stop feature 1420 disposed distally of the body 100. In at least some embodiments, the first stop feature 1410 and/or the second stop feature 1420 may be disposed proximate their respective end of the second suture element 1400. In addition or alternatively, in some embodiments, the body 100 may include first and/or second stop elements, within or formed from the proximal coupler 140 and/or the distal coupler 150 for example, to secure the body 100 to the second suture element 1400. Translation of the elongated sheath 1300 proximally relative to the body 100 may release the body 100 such that the body 100 is radially unconstrained and/or free to assume the expanded or unstressed configuration. In at least some embodiments, in the delivery configuration, the first radially expandable portion 110 is disposed within the lumen of the elongated sheath 1300 in the collapsed configuration and the second radially expandable portion 120 is disposed outside of and/or distal of the elongated sheath 1300 in the expanded configuration. In other words, when using the body 100 in conjunction with the elongated sheath 1300, the delivery configuration may include the body 100 being in a state of partial expansion wherein the second radially expandable portion 120 is in the expanded or unstressed configuration while the first radially expandable portion 110 is in the collapsed configuration. In some embodiments, the suture element 1200 may be disposed through the proximal end of the deployment head 1310. The stop feature 1210 of the suture element 1200 may be disposed proximal of the first radially expandable portion 110 and/or the body 100. In some embodiments, the elongated sheath 1300 may include and/or be formed from a polymeric material, although other biocompatible materials are also contemplated. In some embodiments, the deployment head 1310 may include a tapered proximal end and a reduced outer diameter distal end portion coupled to the elongated sheath 1300. In some embodiments, the deployment head 1310 may include and/or be formed from a metallic material, a polymeric material, a composite material, or other biocompatible materials. In at least some embodiments, the deployment head 1310 and the elongated sheath 1300 may be formed from different materials. Some suitable non-limiting materials for the elongated sheath 1300 and/or the deployment head 1310 are described below.

Figure 14:
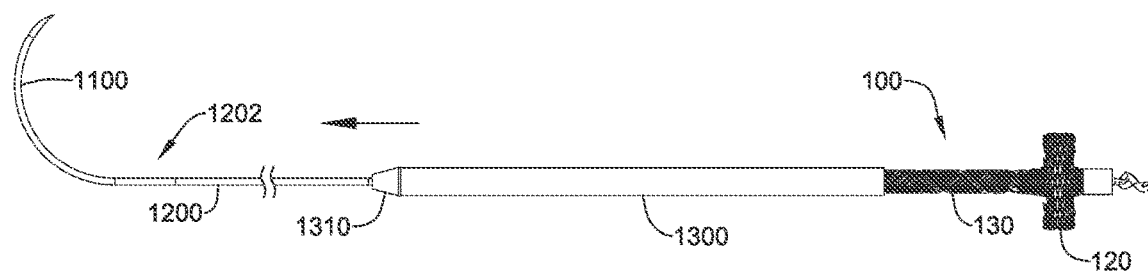
FIGS. 14-17 illustrate an example deployment method of the heart valve anchor apparatus of FIGS. 13-13A.
Figure 15:
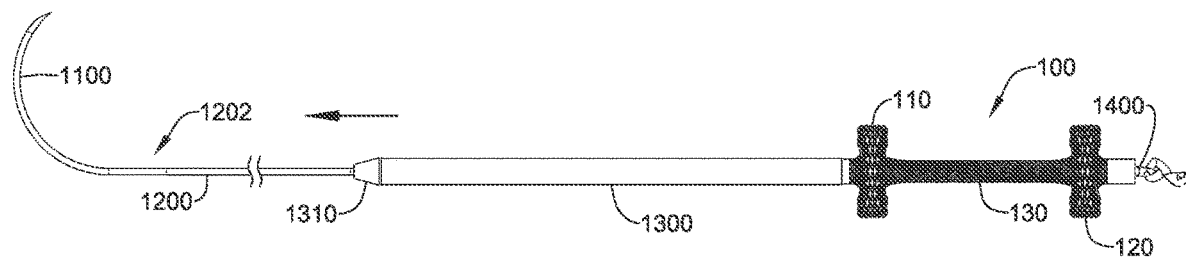
Figure 16:
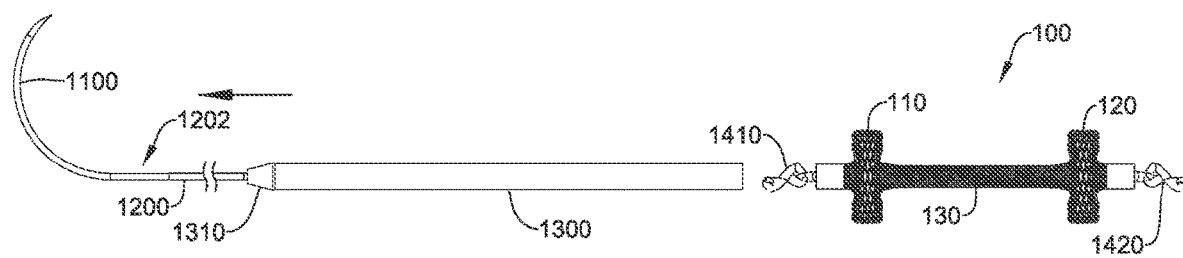
Figure 17:
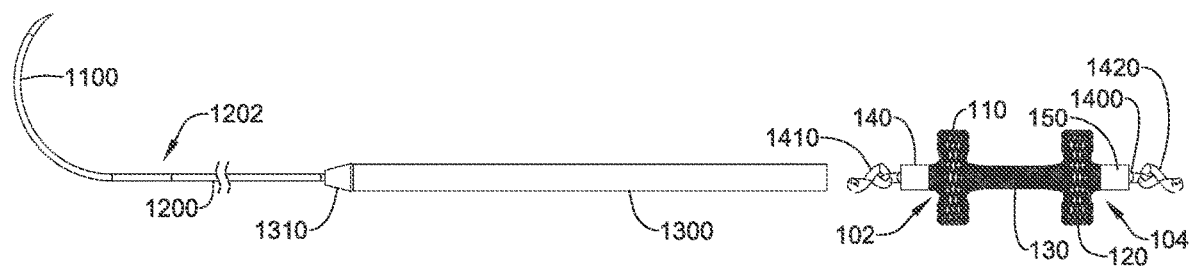

FIGS. 14-17 illustrate different stages of an example "automatic" method of deploying a heart valve anchor apparatus using the heart valve anchor apparatus and/or the tissue penetrating device of FIGS. 13 and 13A. In FIG. 13, a body 100 is at least partially disposed within the elongated sheath 1300. The suture element 1200 extends proximally from the deployment head 1310 to the needle 1100. The needle 1100 may be adapted and configured to be grasped by a user's hand to guide the needle 1100 through tissue and/or to thereafter pull the needle 1100, the suture element 1200, the elongated sheath 1300, and/or the body 100 through and/or into engagement with the tissue. In FIG. 14, the needle 1100 and the suture element 1200 have been pulled proximally relative to the body 100. Pulling the suture element 1200 proximally engages the stop feature 1210 against a distally-facing wall at and/or within the proximal end of the deployment head 1310. Further proximal translation of the needle 1100 and/or the suture element 1200 relative to the body 100 pulls the elongated sheath 1300 proximally relative to the body 100 to partially expose the root portion 130 of the body 100 in addition to the second radially expandable portion 120. In FIG. 15, the first radially expandable portion 110 has been released from the elongated sheath 1300 and has expanded to the expanded or unstressed configuration with the second suture element 1400 extending through the body 100. Additional proximal translation of the needle 1100 and/or the suture element 1200 relative to the body 100 then separates the elongated sheath 1300 from the body 100. The suture element 1200 remains disposed through the deployment head 1310 and attached to the needle 1100 while the second suture element 1400 extends through the body 100, as seen in FIG. 16 for example. Upon separating the elongated sheath 1300 from the body 100, the body 100 is completely released from the tissue penetrating device. In some embodiments, the body 100 may then be manually manipulated from the expanded or unstressed configuration toward and/or into a shortened configuration, as shown in FIG. 17, by applying tension to a distal portion of the second suture element 1400 while a proximally-directed force is applied to the distal portion 104 of the body 100 and/or by applying tension to a proximal portion of the second suture element 1400 while a distally-directed force is applied to the proximal portion 102 of the body 100. In the shortened configuration, the first radially expandable portion 110 and the second radially expandable portion 120 are closer together than in the expanded or unstressed configuration. In some embodiments, the root portion 130 may be longitudinally compressed and/or shortened in the shortened configuration. In some embodiments, an outer extent of the root portion 130 may expand radially up to or as far as the outer extent of the first radially expandable portion 110 and/or the second radially expandable portion 120 as the body 100 and/or the root portion 130 is compressed and/or shortened longitudinally. In other words, in some embodiments, a maximum outer extent of the root portion 130 may increase as the length of the root portion 130 is decreased. A stop element, within or formed from the proximal coupler 140 and/or the distal coupler 150 for example, may secure the body 100 to the second suture element 1400 and retain the body 100 in the shortened configuration.

Figure 18:
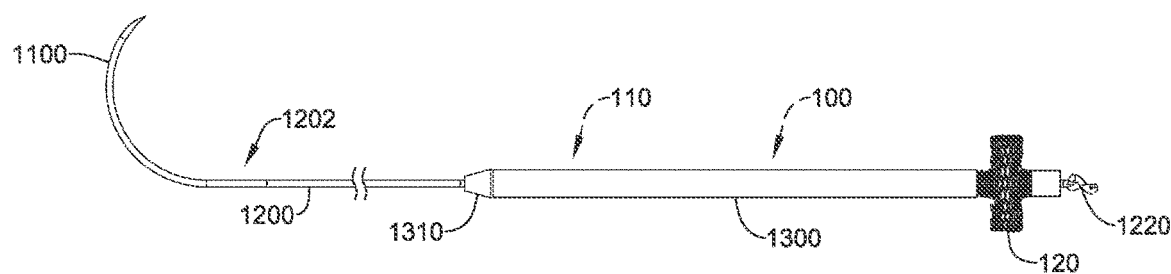
FIGS. 18-18A illustrate an example heart valve anchor apparatus.
Figure 18A:
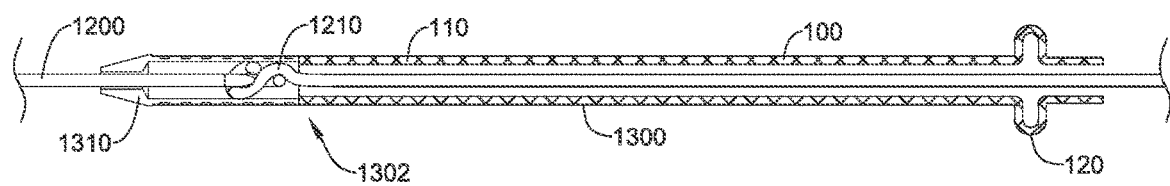

FIGS. 18 and 18A illustrate an example heart valve anchor apparatus including a body 100 housed at least partially within an example tissue penetrating device, such as an elongated sheath 1300, in a delivery configuration. In some embodiments, the heart valve anchor apparatus may include a needle 1100, a suture element 1200 having a proximal end 1202 attached to the needle 1100, and an elongated sheath 1300 having a deployment head 1310 fixedly attached at a proximal end 1302 of the elongated sheath 1300. The elongated sheath 1300 and/or the deployment head 1310 may include a lumen extending therethrough. The suture element 1200 may pass distally into the lumen of the deployment head 1310 and may have or include a stop feature 1210 disposed within the deployment head 1310. The body 100 may be at least partially disposed within the lumen of the elongated sheath 1300 and/or a portion of the body 100 may extend distally from the lumen of the elongated sheath 1300. Translation of the elongated sheath 1300 proximally relative to the body 100 may release the body 100 such that the body 100 is radially unconstrained and/or free to assume the expanded or unstressed configuration. In at least some embodiments, in the delivery configuration, the first radially expandable portion 110 is disposed within the lumen of the elongated sheath 1300 in the collapsed configuration and the second radially expandable portion 120 is disposed outside of and/or distal of the elongated sheath 1300 in the expanded configuration. When using the body 100 in conjunction with the elongated sheath 1300, the delivery configuration may include the body 100 being in a state of partial expansion wherein the second radially expandable portion 120 is in the expanded or unstressed configuration while the first radially expandable portion 110 is in the collapsed configuration. In some embodiments, the suture element 1200 may be disposed through the body 100 along the longitudinal centerline. The stop feature 1210 of the suture element 1200 may be disposed proximal of the first radially expandable portion 110 and/or the body 100. In some embodiments, the suture element 1200 may include an additional stop feature 1220 disposed distal of the second radially expandable portion 120 and/or the body 100. In some embodiments, the elongated sheath 1300 may include and/or be formed from a polymeric material, although other biocompatible materials are also contemplated. In some embodiments, the deployment head 1310 may include a tapered proximal end and a reduced diameter distal end portion coupled to the elongated sheath 1300. In some embodiments, the deployment head 1310 may include and/or be formed from a metallic material, a polymeric material, a composite material, or other biocompatible materials. Some suitable non-limiting materials for the elongated sheath 1300 and/or the deployment head 1310 are described below.

Figure 19:
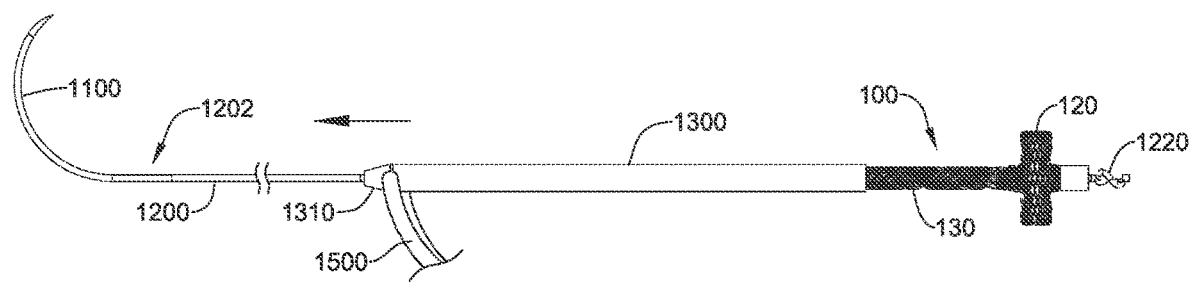
FIGS. 19-22 illustrate an example deployment method of the heart valve anchor apparatus of FIGS. 18-18A.
Figure 20:
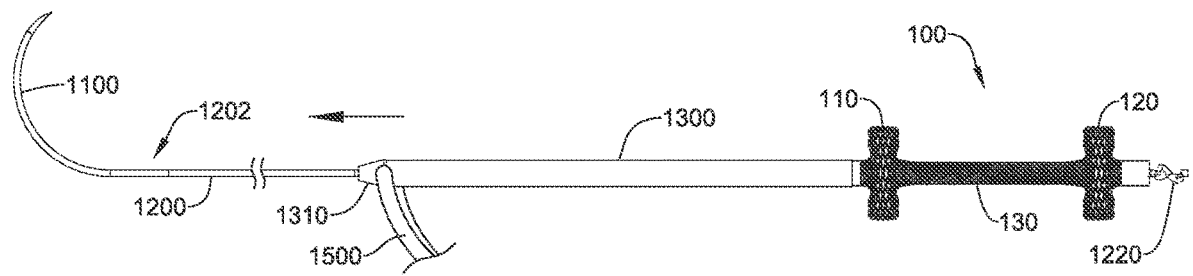
Figure 21:
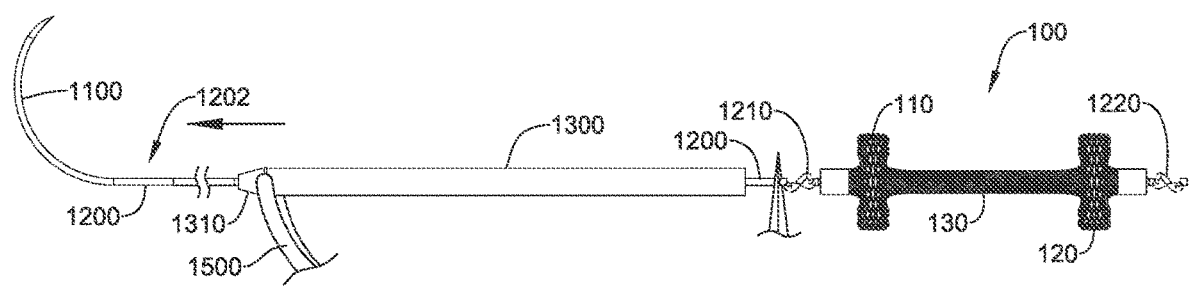
Figure 22:
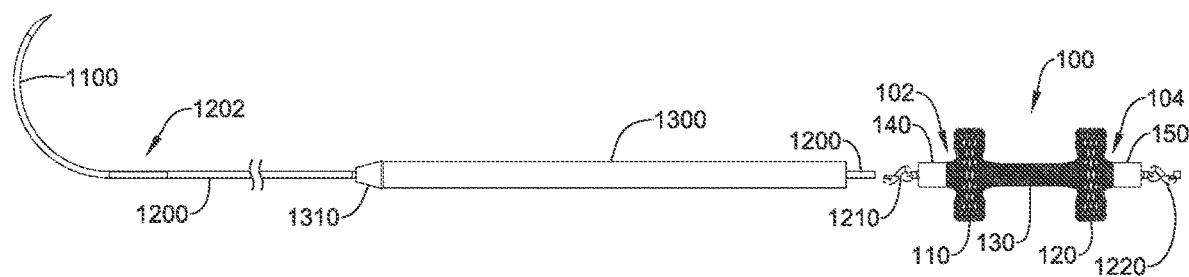

FIGS. 19-22 illustrate different stages of an example "manual" method of deploying a heart valve anchor apparatus using the heart valve anchor apparatus and/or the tissue penetrating device of FIGS. 18 and 18A. In FIG. 18, a body 100 is at least partially disposed within the elongated sheath 1300. The suture element 1200 extends proximally from the deployment head 1310 to the needle 1100. The needle 1100 may be adapted and configured to be grasped by a user's hand to guide the needle 1100 through tissue and/or to thereafter pull the needle 1100, the suture element 1200, the elongated sheath 1300, and/or the body 100 through and/or into engagement with the tissue. After engaging the second radially expandable portion 120 against the tissue, the elongated sheath 1300 may be pulled proximally relative to the body 100 (and/or the suture element 1200) by grasping the deployment head 1310 with a forceps 1500, as seen in FIG. 19 for example. Further proximal translation of the deployment head 1310 and/or the forceps 1500 relative to the body 100 and/or the suture element 1200 pulls the elongated sheath 1300 proximally relative to the body 100 and/or the suture element 1200 to partially expose the root portion 130 of the body 100 in addition to the second radially expandable portion 120. In FIG. 20, the first radially expandable portion 110 has been released from the elongated sheath 1300 and has expanded to the expanded or unstressed configuration. Additional proximal translation of the elongated sheath 1300, the deployment head 1310, and/or the forceps 1500 relative to the body 100 and/or the suture element 1200 then separates the elongated sheath 1300 from the body 100. The suture element 1200 remains disposed through the body 100 and extends into and through the elongated sheath 1300 to the needle 1100 until the suture element 1200 is severed, broken, or cut, as seen in FIG. 21 for example. Upon releasing, severing, breaking, or cutting the suture element 1200, the body 100 is completely released from the tissue penetrating device. In some embodiments, the body 100 may then be manually manipulated from the expanded or unstressed configuration toward and/or into a shortened configuration, as shown in FIG. 22, by applying tension to a distal portion of the suture element 1200 while a proximally-directed force is applied to the distal portion 104 of the body 100 and/or by applying tension to a proximal portion of the suture element 1200 while a distally-directed force is applied to the proximal portion 102 of the body 100. In the shortened configuration, the first radially expandable portion 110 and the second radially expandable portion 120 are closer together than in the expanded or unstressed configuration. In some embodiments, the root portion 130 may be longitudinally compressed and/or shortened in the shortened configuration. In some embodiments, an outer extent of the root portion 130 may expand radially up to or as far as the outer extent of the first radially expandable portion 110 and/or the second radially expandable portion 120 as the body 100 and/or the root portion 130 is compressed and/or shortened longitudinally. In other words, in some embodiments, a maximum outer extent of the root portion 130 may increase as the length of the root portion 130 is decreased. A stop element, within or formed from the proximal coupler 140 and/or the distal coupler 150 for example, may secure the body 100 to the suture element 1200 and retain the body 100 in the shortened configuration.

Figure 23:
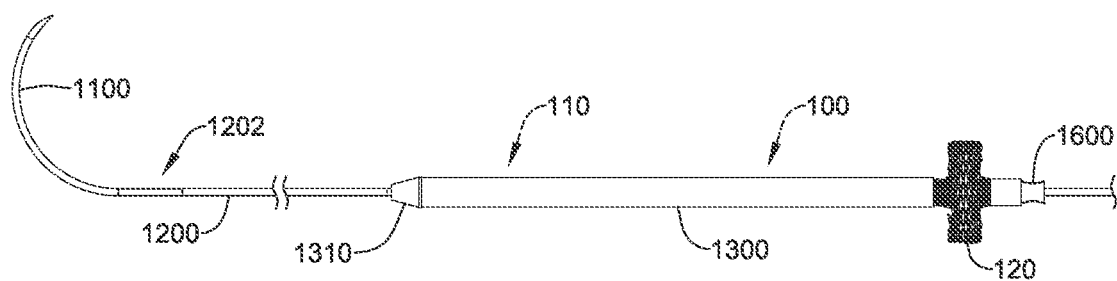
FIGS. 23-23A illustrate an example heart valve anchor apparatus.
Figure 23A:
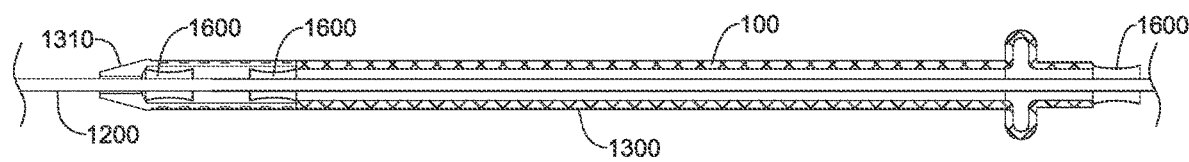

FIGS. 23 and 23A illustrate an example heart valve anchor apparatus including a body 100 housed at least partially within an example tissue penetrating device, such as an elongated sheath 1300, in a delivery configuration, similar to the heart valve anchor apparatus of FIGS. 13 and 18. FIGS. 13 and 18, for example, are shown with stop feature 1210, 1220, 1410, 1420 comprising a knot in the suture element(s) 1200, 1400. However, other stop features are also contemplated. For example, the heart valve anchor apparatus of FIGS. 23 and 23A makes use of alternative stop features comprising tubular element(s) 1600 crimped onto the suture element 1200 and/or the second suture element 1400. In various embodiments of a heart valve anchor apparatus, different embodiments of the stop feature(s) 1210, 1220, 1410, 1420, 1600 may be used and/or interchanged as desired. For example, in some embodiments, one stop feature may be a knot while another stop feature may be a tubular element. Other alternatives, configurations, and/or combinations are also contemplated. The tubular element 1600 may be made from any suitable biocompatible material. Some examples of suitable materials are discussed below.

Figure 24:
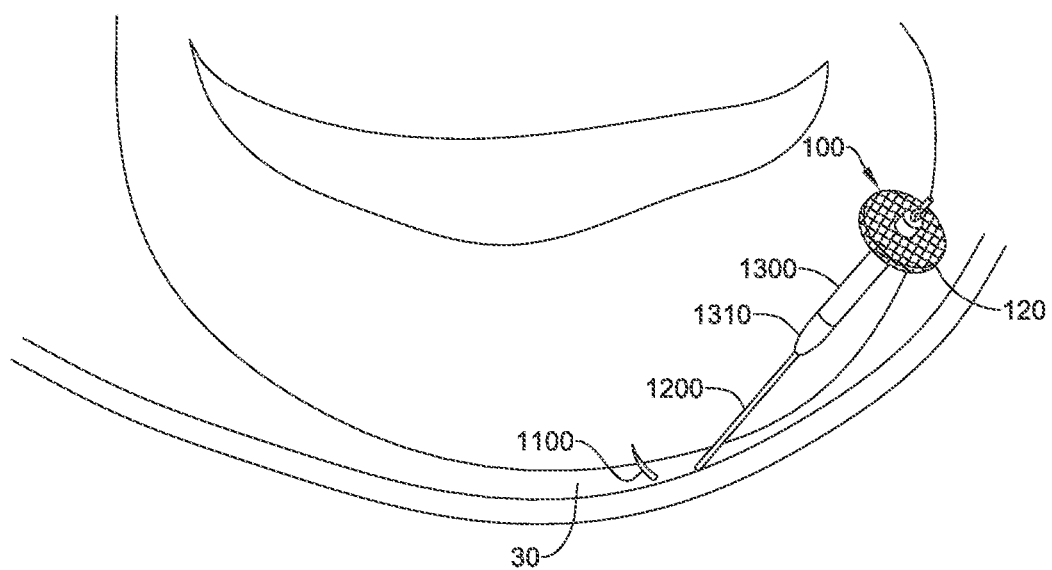
FIGS. 24-28 illustrate an example deployment of a heart valve anchor apparatus within a heart valve annulus.
Figure 25:
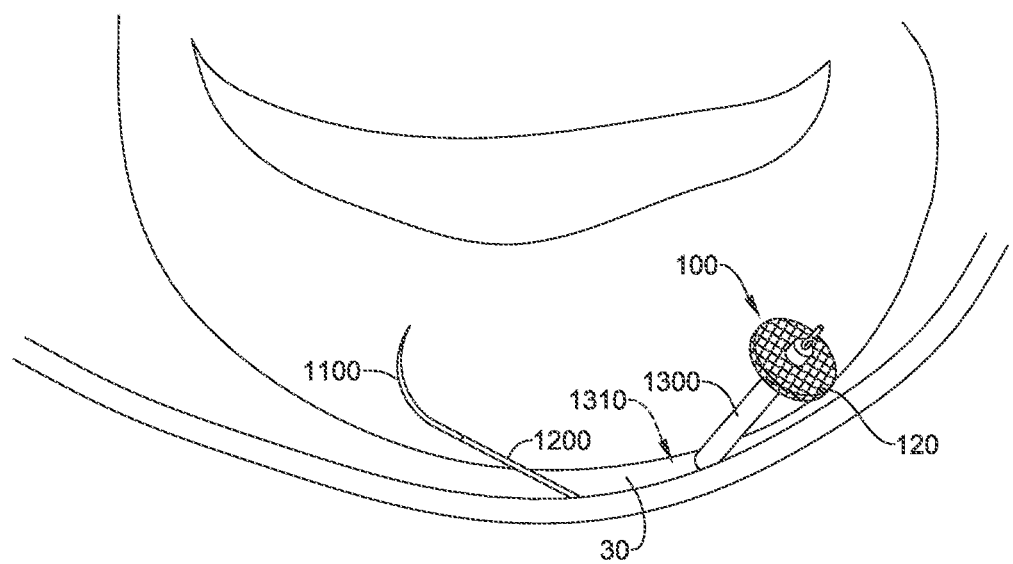
Figure 26:
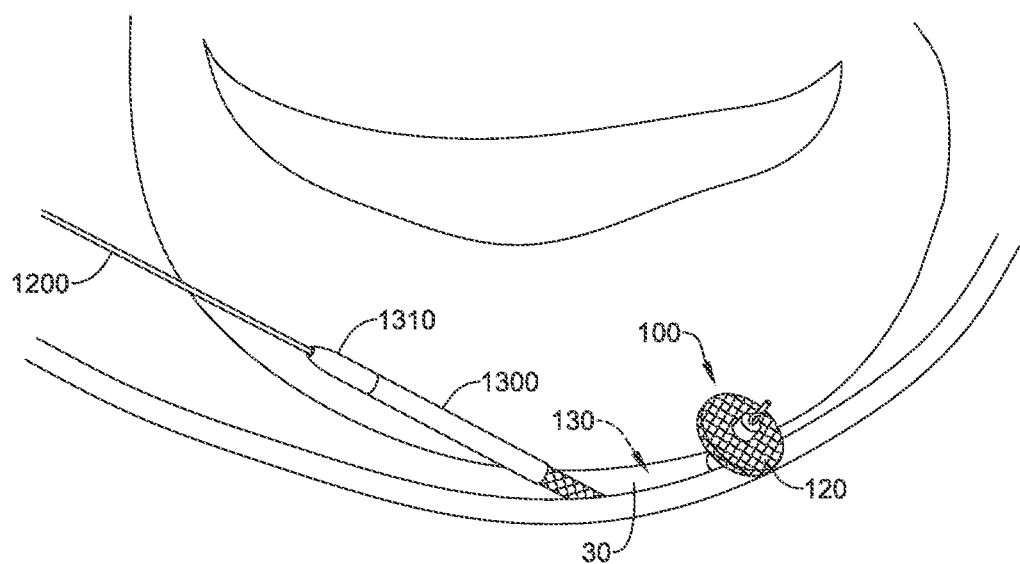
Figure 27:
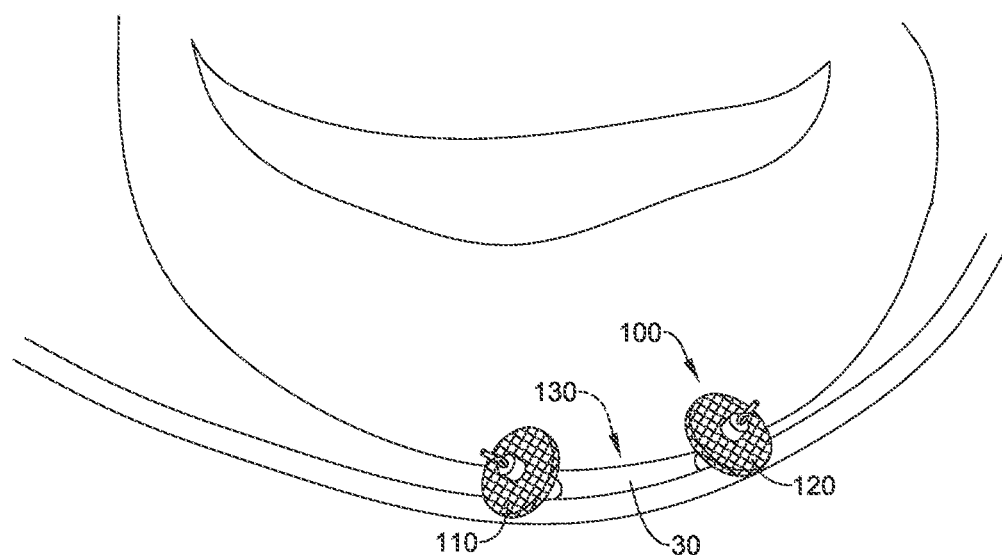
Figure 28:
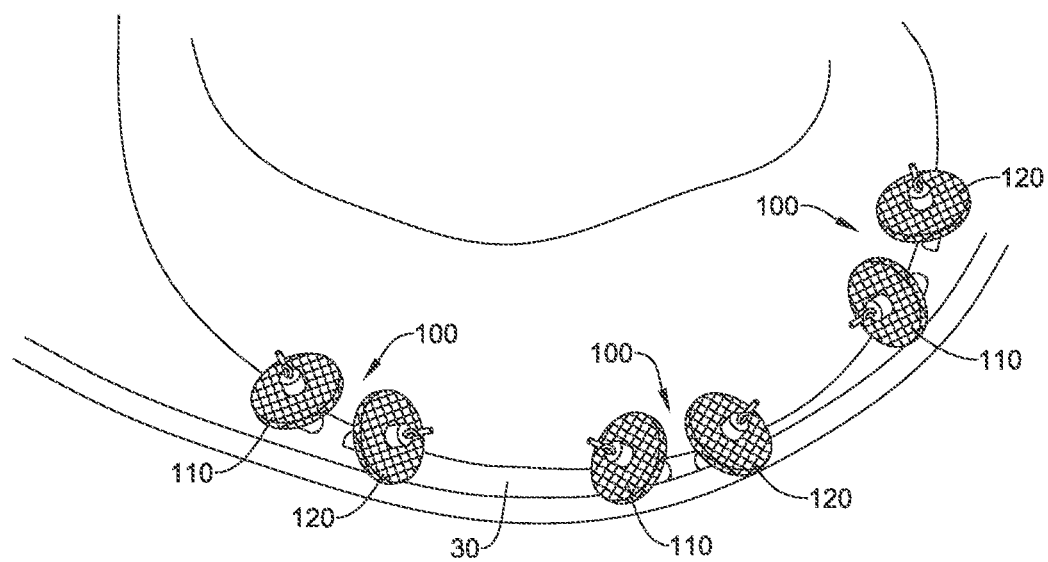

FIGS. 24-28 illustrate example methods of deploying a heart valve anchor apparatus using the heart valve anchor apparatus and/or the tissue penetrating device of FIGS. 13-23. FIGS. 24-28 apply similarly to the two different configurations and/or methods of deploying a heart valve anchor apparatus discussed above. As seen in FIG. 24, a tissue penetrating device may be directed into tissue 30 of a heart valve annulus (e.g., an annulus of the tricuspid valve 12, the pulmonary valve 14, the aortic valve 16, or the mitral valve 18). It is to be noted that while a bicuspid heart valve having two valve leaflets (e.g., the mitral valve 18, etc.) is illustrated in the figures, the same method may be applied to a heart valve having three valve leaflets (e.g., the pulmonary valve 14, the tricuspid valve 12, the aortic valve 16, etc.). The method may also be applied from either the upstream side or the downstream side of the heart valve, depending upon the approach used (e.g., surgical, intravascular, subclavian, aortic, femoral, arterial, venous, etc.). The tissue penetrating device, for example the needle 1100, may be directed into the tissue 30 from a first side of the heart valve annulus, through the tissue 30, and back out the first side of the heart valve annulus, as seen in FIG. 24. In some embodiments, this process may be repeated one or more additional times to pass the tissue penetrating device through additional tissue 30, thereby forming one or more plications of tissue. In other words, the tissue penetrating device may be zig-zagged through the tissue 30 and/or take a non-linear path through the tissue 30 before the body 100 is released and/or transitioned from the delivery or compressed configuration to the expanded or unstressed configuration. Additional details related to the passage and/or path of the heart valve anchor apparatus through the tissue 30 will be discussed below. After the needle 1100 has passed through the tissue 30, the needle 1100 and/or the suture element 1200 may be pulled proximally away from the tissue 30 as discussed above until the deployment head 1310 of the elongated sheath 1300 engages the tissue 30, as seen in FIG. 25. Proximal translation of the needle 1100 and/or the suture element 1200 may pull the deployment head 1310 and/or the elongated sheath 1300 through the tissue 30 and engage the second radially expandable portion 120 of the body 100 against the tissue 30 of the heart valve annulus. From this point, the deployment head 1310 of the elongated sheath 1300 is pulled away (e.g., translated proximally relative to the body 100) from the second radially expandable portion 120 using one of the methods described above, thereby releasing the root portion 130 within the tissue 30, as seen in FIG. 26, and the first radially expandable portion 110 outside of the tissue 30, as seen in FIG. 27, such that the first radially expandable portion 110 and the second radially expandable portion 120 both engage the tissue 30 disposed between them in the unstressed configuration. In some embodiments, the suture element 1200 (if still present, depending on the method of deployment used) may be severed, broken, or cut to release the body 100. In some embodiments, the body 100 may be transitioned from the expanded or unstressed configuration toward and/or to the shortened configuration, as shown in FIG. 28 for example, in one of the methods or steps described above. In the unstressed and/or shortened configuration, the tissue 30 may be compressed between the first radially expandable portion 110 and the second radially expandable portion 120.

In any given method or application of the heart valve anchor apparatus, at least one heart valve anchor apparatus may be deployed within a heart valve annulus. In some example, the at least one heart valve anchor apparatus may include two, three, four, or more heart valve anchor apparatus deployed within the heart valve annulus as necessary to sufficiently reduce, tighten, and/or contract the heart valve annulus to bring the free edges of the heart valve leaflets back into apposition when the heart valve is closed. In some embodiments, at least one heart valve anchor apparatus may be deployed within or adjacent the annulus of one, more than one, or each cusp or leaflet of the heart valve being treated. It has been found that the body of the heart valve anchor apparatus may sufficiently influence the tissue of the heart valve annulus to resolve heart valve regurgitation in the expanded or unstressed configuration, or the body of the heart valve anchor apparatus may be transitioned to the shortened configuration when additional influence is needed to resolve heart valve regurgitation.

Figure 29:
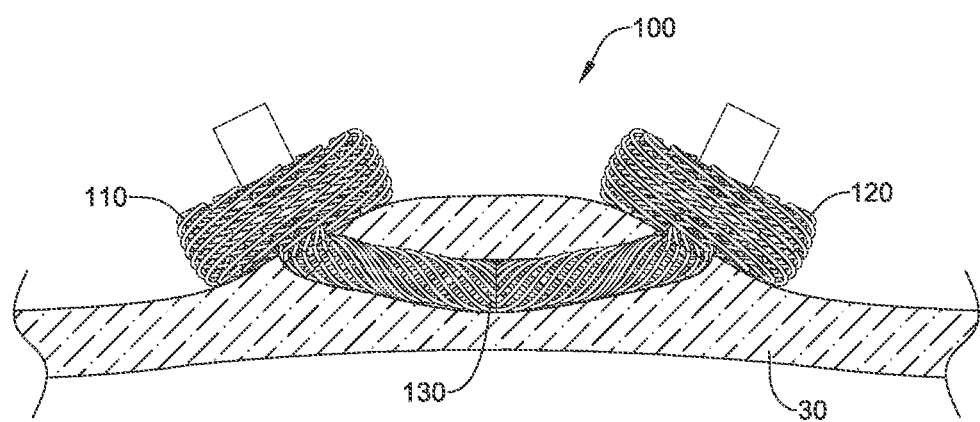
FIGS. 29-30A illustrate example configurations of a heart valve anchor apparatus deployed within a heart valve annulus according to the methods of FIGS. 14-17 and/or 19-22.

FIG. 29 illustrates an example passage and/or method of a tissue penetrating device through the tissue 30 of the heart valve annulus. For convenience, the configuration of FIG. 29 may be referred to as the "tunneling" method. In the "tunneling" method, the heart valve anchor apparatus may be passed into the tissue 30 from a first side of the heart valve annulus, extend generally laterally within the tissue 30 of the heart valve annulus without passing completely through a second opposing side of the heart valve annulus (e.g., the root portion 130 of the heart valve anchor apparatus remains within the "wall" or "thickness" of the tissue 30 of the heart valve annulus), and then the heart valve anchor apparatus is passed back through to the first side of the heart valve annulus, thereby forming a "tunnel" through the tissue 30 which has opposing ends both opening to the same (e.g., first) side of the heart valve annulus. In the "tunneling" method, both the first radially expandable portion 110 and the second radially expandable portion 120 engage the tissue 30 on the first side of the heart valve annulus.

Figure 29A:
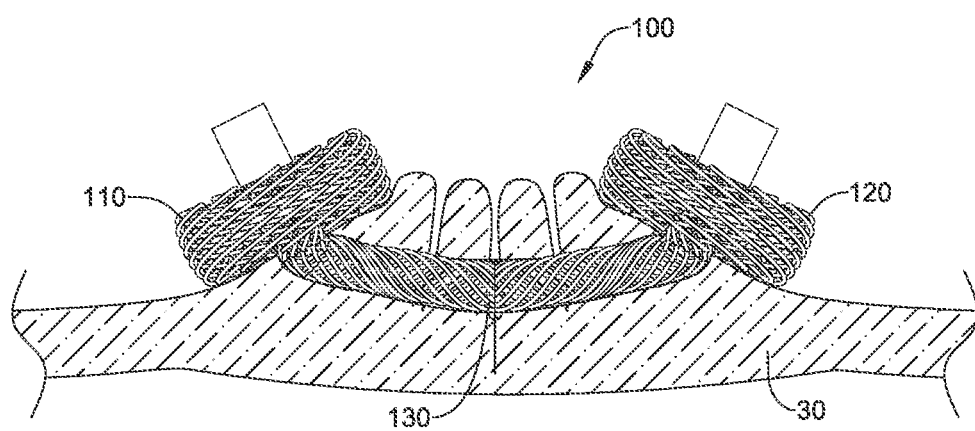

FIG. 29A illustrates an example passage and/or method of a tissue penetrating device through the tissue 30 of the heart valve annulus. FIG. 29A illustrates the same "tunneling" method shown in FIG. 29, wherein the tissue penetrating device has been passed through the tissue 30 multiple times (e.g., zig-zagged or forming a non-linear path through the tissue 30), thereby forming one or more plications of tissue 30 formed between the first radially expandable portion 110 and the second radially expandable portion 120.

Figure 30:
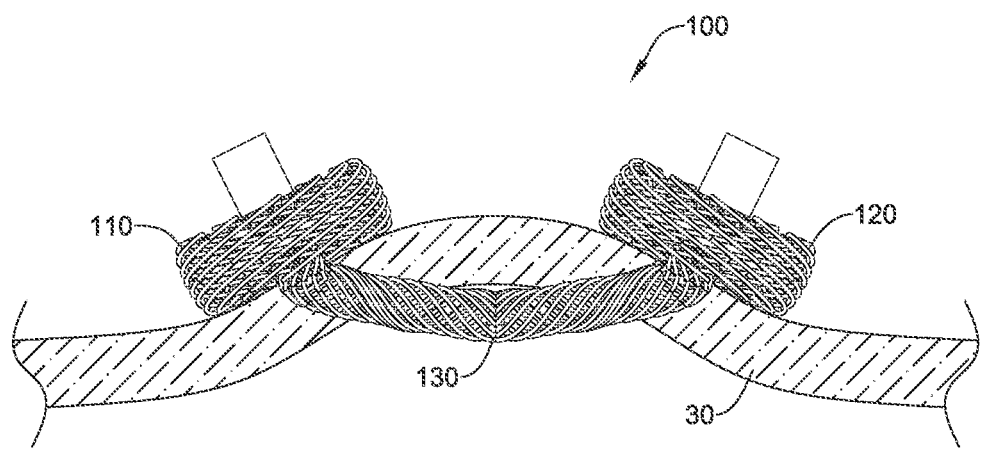

FIG. 30 illustrates another example passage and/or method of a tissue penetrating device through the tissue 30 of the heart valve annulus. For convenience, the configuration of FIG. 30 may be referred to as the "U" method. In the "U" method, the heart valve anchor apparatus may be passed into the tissue 30 from a first side of the heart valve annulus, extend generally through the tissue 30 of the heart valve annulus and passing completely through a second opposing side of the heart valve annulus (e.g., the root portion 130 of the heart valve anchor apparatus passes through the "wall"

or "thickness" of the tissue 30 of the heart valve annulus), the heart valve anchor apparatus is passed generally laterally alongside the second opposing side of the heart valve annulus, and then the heart valve anchor apparatus is passed back into the tissue 30 from the second side of the heart valve annulus, extending generally through the tissue 30 of the heart valve annulus and passing completely through back to the first side of the heart valve annulus, thereby forming two passages through the tissue 30 which each have opposing ends opening on different sides of the heart valve annulus. In the "U" method, both the first radially expandable portion 110 and the second radially expandable portion 120 engage the tissue 30 on the first side of the heart valve annulus. In the "U" method, the root portion 130 passes through the tissue 30 from the first side of the heart valve annulus to the second side of the heart valve annulus, extends laterally alongside the tissue 30 proximate the second side of the heart valve annulus, and passes back through the tissue 30 from the second side of the heart valve annulus to the first side of the heart valve annulus. In this example, each heart valve anchor apparatus passes completely through the tissue 30 in two different locations.

Figure 30A:
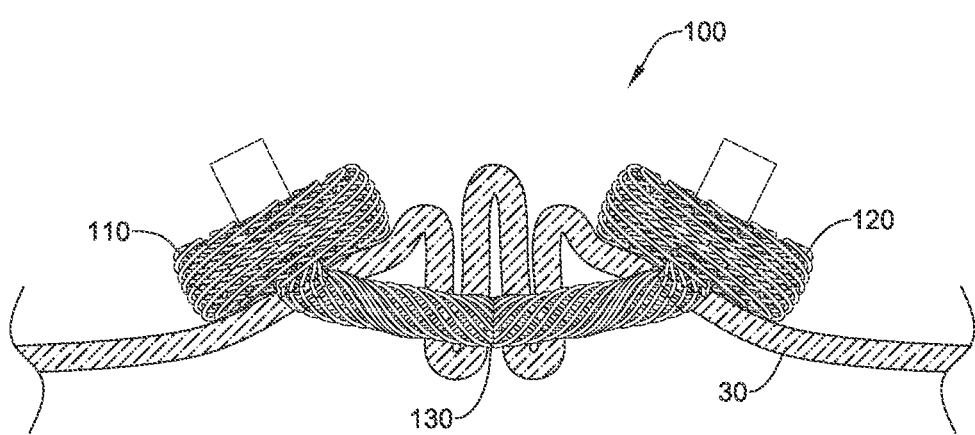

FIG. 30A illustrates an example passage and/or method of a tissue penetrating device through the tissue 30 of the heart valve annulus. FIG. 30A illustrates the same "U" method shown in FIG. 30, wherein the tissue penetrating device has been passed through the tissue 30 multiple times (e.g., zig-zagged or forming a non-linear path through the tissue 30), thereby forming one or more plications of tissue 30 formed between the first radially expandable portion 110 and the second radially expandable portion 120.

Figure 31:
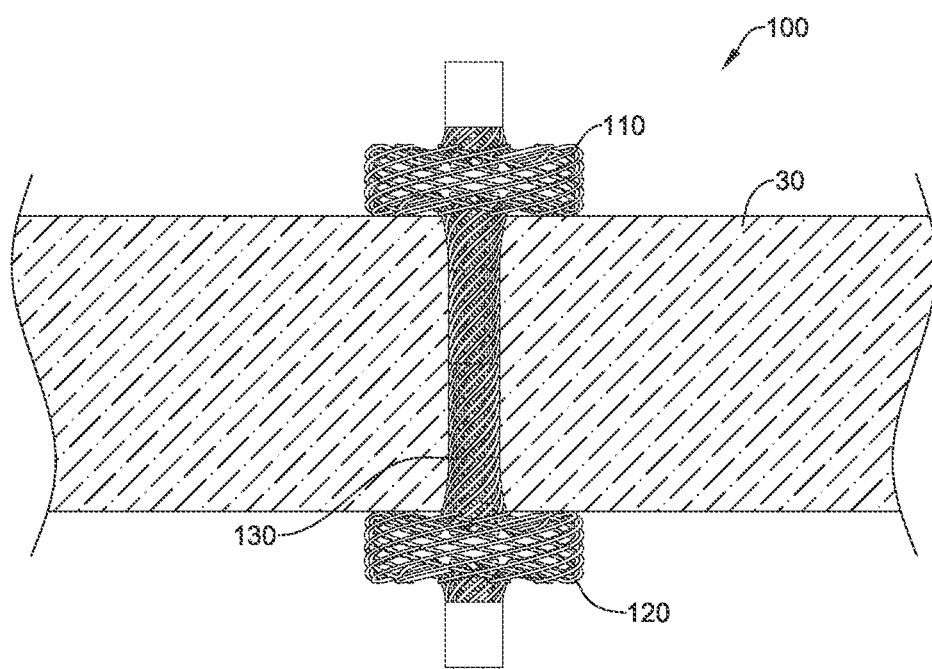
FIG. 31 illustrates an example configuration of a heart valve anchor apparatus within a heart valve annulus.
Figure 32:
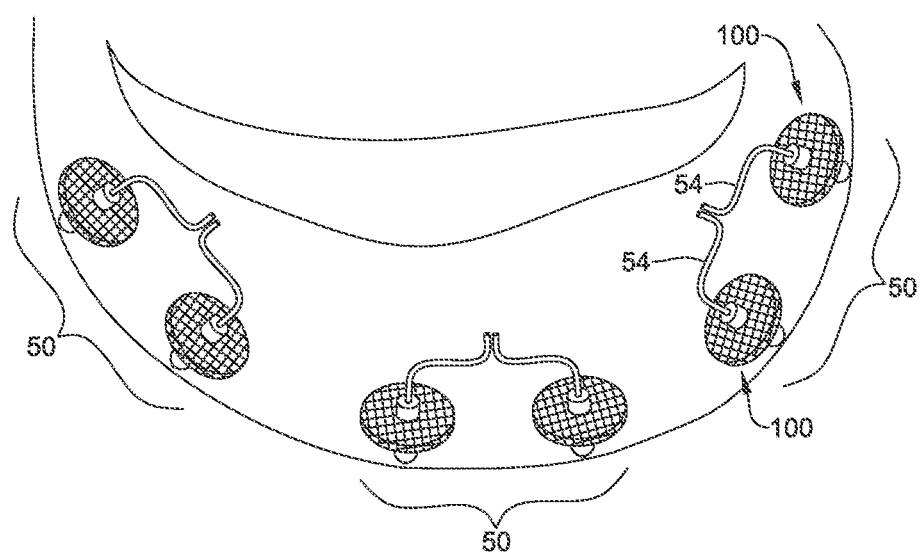
FIGS. 32-33 illustrate an example deployment of a heart valve anchor apparatus within a heart valve annulus using the configuration of FIG. 31.
Figure 33:
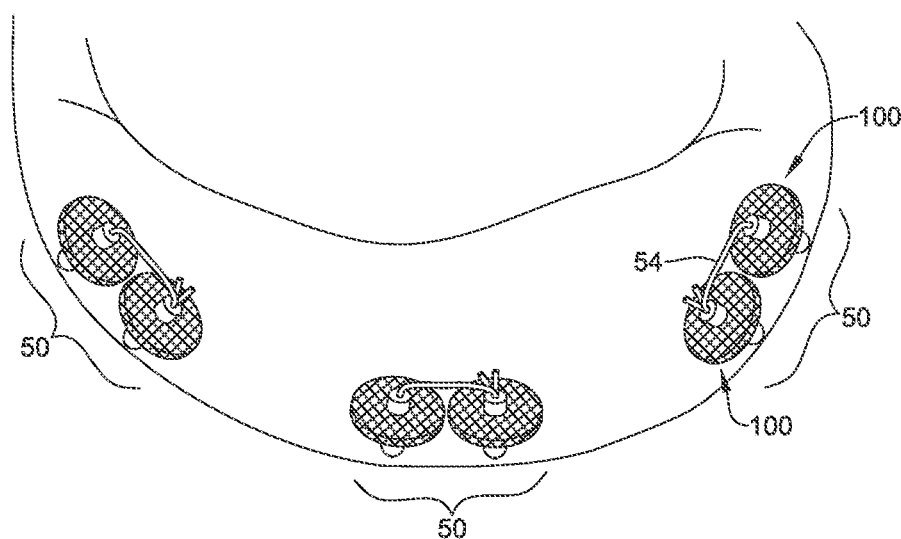

FIG. 31 illustrates another example passage and/or method of a heart valve anchor apparatus disposed within the tissue 30 of the heart valve annulus. For convenience, the configuration of FIG. 31 may be referred to as the "trans-annular" method. In the "trans-annular" method, the heart valve anchor apparatus may be passed into the tissue 30 from a first side of the heart valve annulus, extend generally through the tissue 30 of the heart valve annulus, and pass completely through to a second opposing side of the heart valve annulus (e.g., the root portion 130 of the heart valve anchor apparatus passes through the "wall" or "thickness" of the tissue 30 of the heart valve annulus), thereby forming a single passage through the tissue 30 which has opposing ends opening on different sides of the heart valve annulus. In this example, each heart valve anchor apparatus passes completely through the tissue 30 at one location. In the "trans-annular" method, the first radially expandable portion 110 and the second radially expandable portion 120 engage the tissue 30 on opposite sides of the heart valve annulus. In other words, the first radially expandable portion 110 may engage the tissue 30 on the first side of the heart valve annulus and the second radially expandable portion 120 may engage the tissue 30 on the second side of the heart valve annulus. In practice, the "trans-annular" method may sometimes (although it is not required to) utilize pairs of heart valve anchor apparatus and/or bodies 100. For example, as seen in FIGS. 32 and 33, at least one pair 50 of bodies 100 may be disposed within and/or through the tissue 30 of the heart valve annulus. Each one of the bodies 100 of the pair 50 may include a suture element 54 extending through the body 100. After deploying each one of the bodies 100 of the pair 50, the suture element(s) 54 extending from each body 100 may be fastened (e.g., tied, glued, melted, etc.) together to draw the pair 50 of bodies 100 closer together, thereby reducing, tightening, and/or contracting the heart valve annulus to bring the free edges of the heart valve leaflets back into apposition when the heart valve is closed.

Figure 34:
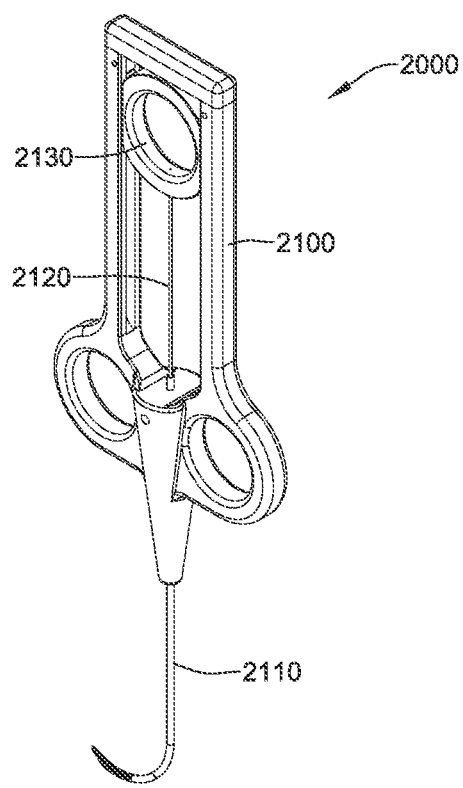
FIGS. 34-36 illustrate example deployment tools for a heart valve anchor apparatus.
Figure 35:
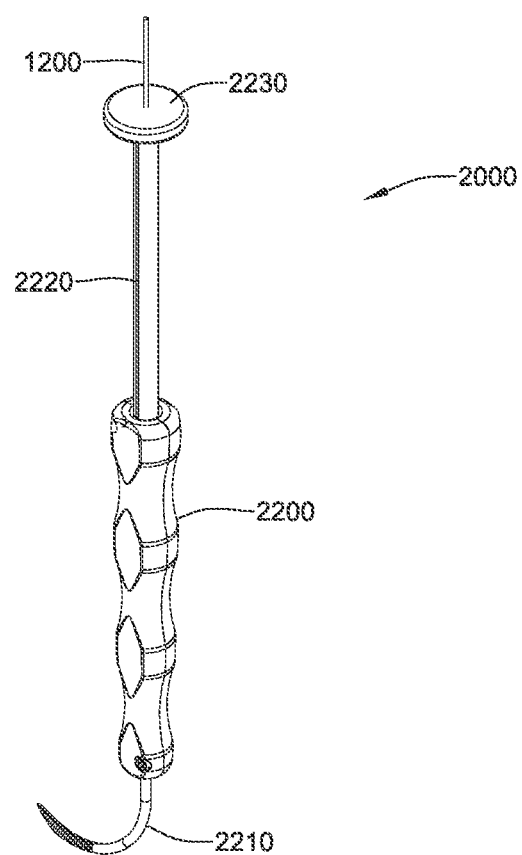
Figure 36:
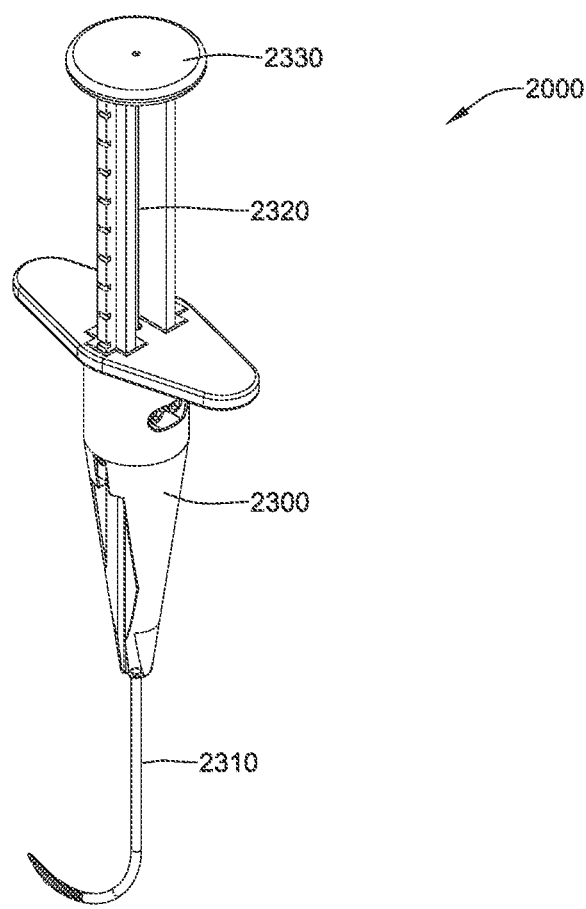

FIGS. 34-36 illustrate example tissue penetrating devices, which may include various configurations of a delivery tool 2000. It is to be understood that these configurations are merely exemplary, and other configurations are also contemplated. The skilled person will recognize that variation of these configurations, as well as different configurations, may also be used with the apparatus of the current disclosure.

The delivery tool 2000 of FIG. 34 may include a handle 2100 having a "cigar cutter" configuration. In some embodiments, the handle 2100 may include a hollow, tubular needle 2110 extending distally therefrom. A heart valve anchor apparatus may include a body 100 (not shown) disposed within the needle 2110 in a delivery configuration. In some embodiments, a tubular member may extend between and/or connect the handle 2100 and the needle 2110. A push rod 2120 may extend proximally from the body 100 within the needle 2110 and/or the handle 2100. The push rod 2120 may connect and/or be fixedly attached to a movable actuator element 2130. The actuator element 2130 may be axially and/or longitudinally slidable relative to a body of the handle 2100. The actuator element 2130 may be configured and/or adapted to permit a user to actuate the handle 2100 with one hand. Axial translation of the actuator element 2130 may result in corresponding axial translation of the push rod 2120 within the needle 2110. Distal axial translation of the actuator element 2130 and/or the push rod 2120 may release the body 100 from the distal end of the needle 2110. In at least some embodiments, the handle 2100 may accommodate the suture element 1200 (not shown) extending therethrough from the body 100.

The delivery tool 2000 of FIG. 35 may include a handle 2200 having a "pen" configuration. In some embodiments, the handle 2200 may include a hollow, tubular needle 2210 extending distally therefrom. A heart valve anchor apparatus may include a body 100 (not shown) disposed within the needle 2210 in a delivery configuration. In some embodiments, a tubular member may extend between and/or connect the handle 2200 and the needle 2210. A push rod 2220 may extend proximally from the body 100 within the needle 2210 and/or the handle 2200. The push rod 2220 may connect and/or be fixedly attached to a movable actuator element 2230. The actuator element 2230 may be axially and/or longitudinally slidable relative to a body of the handle 2200. In some embodiments, the actuator element 2230 may be configured and/or adapted to permit a user to actuate the handle 2200 with one hand. In some embodiments, the actuator element 2230 may be configured and/or adapted to permit a user to actuate the handle 2200 with two hands. Axial translation of the actuator element 2230 may result in corresponding axial translation of the push rod 2220 within the needle 2210. Distal axial translation of the actuator element 2230 and/or the push rod 2220 may release the body 100 from the distal end of the needle 2210. In at least some embodiments, the handle 2200 may accommodate the suture element 1200 extending therethrough from the body 100.

The delivery tool 2000 of FIG. 36 may include a handle 2300 having a "syringe" configuration. In some embodiments, the handle 2300 may include a hollow, tubular needle 2310 extending distally therefrom. A heart valve anchor apparatus may include a body 100 (not shown) disposed within the needle 2310 in a delivery configuration. In some embodiments, a tubular member may extend between and/or connect the handle 2300 and the needle 2310. A push rod 2320 may extend proximally from the body 100 within the needle 2310 and/or the handle 2300. The push rod 2320 may connect and/or be fixedly attached to a movable actuator element 2330. The actuator element 2330 may be axially and/or longitudinally slidable relative to a body of the handle 2300. In some embodiments, the actuator element 2330 may be configured and/or adapted to permit a user to actuate the handle 2300 with one hand. In some embodiments, the actuator element 2330 may be configured and/or adapted to permit a user to actuate the handle 2300 with two hands. Axial translation of the actuator element 2330 may result in corresponding axial translation of the push rod 2320 within the needle 2310. Distal axial translation of the actuator element 2330 and/or the push rod 2320 may release the body 100 from the distal end of the needle 2310. In at least some embodiments, the handle 2300 may accommodate the suture element 1200 (not shown) extending therethrough from the body 100.

Figure 37:
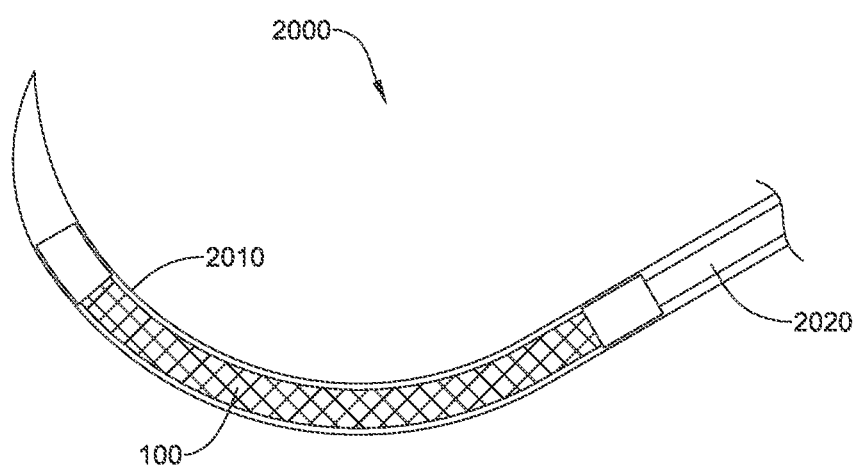
FIG. 37 is a partial cross-sectional schematic view of an example heart valve anchor apparatus disposed within an example deployment tool in a collapsed or delivery configuration.

FIG. 37 is a partial cross-sectional schematic view of an example delivery tool 2000 having a body 100 disposed within a needle 2010 in a delivery configuration. Similar to the delivery tools discussed above, a push rod 2020 may be slidably disposed within the needle 2010 and extend proximally into a body of a handle of the delivery tool 2000 to an actuator element. It will be appreciated that any of the above-described delivery tools 2000 may permit and/or utilize this arrangement for the delivery of the body 100 of a heart valve anchor apparatus.

Figure 38:
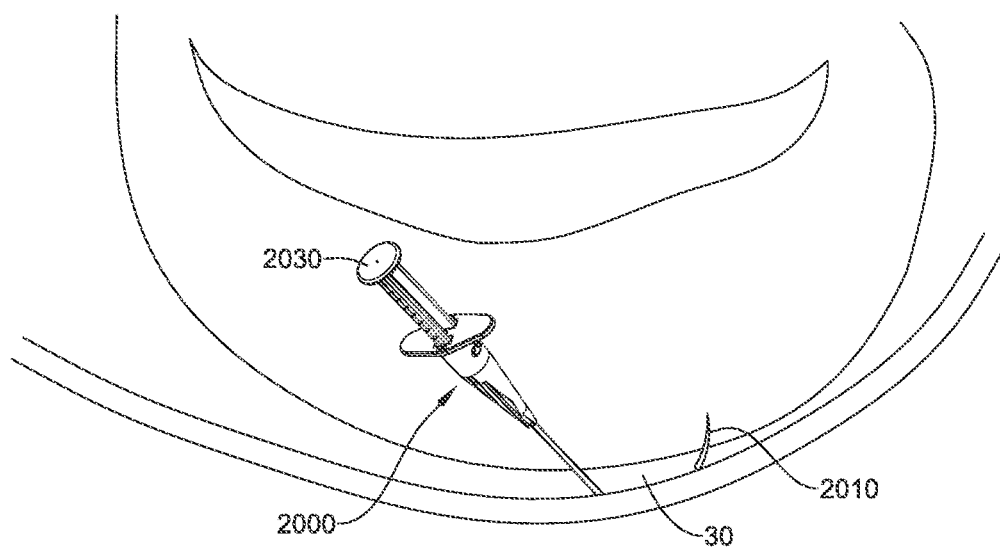
FIGS. 38-41 illustrate an example deployment of a heart valve anchor apparatus using an example deployment tool.
Figure 39:
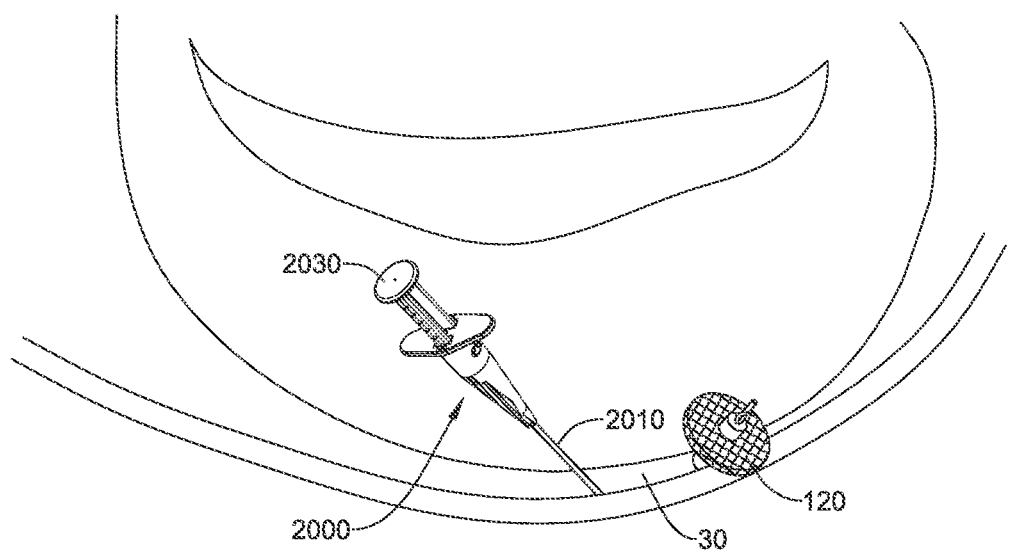
Figure 40:
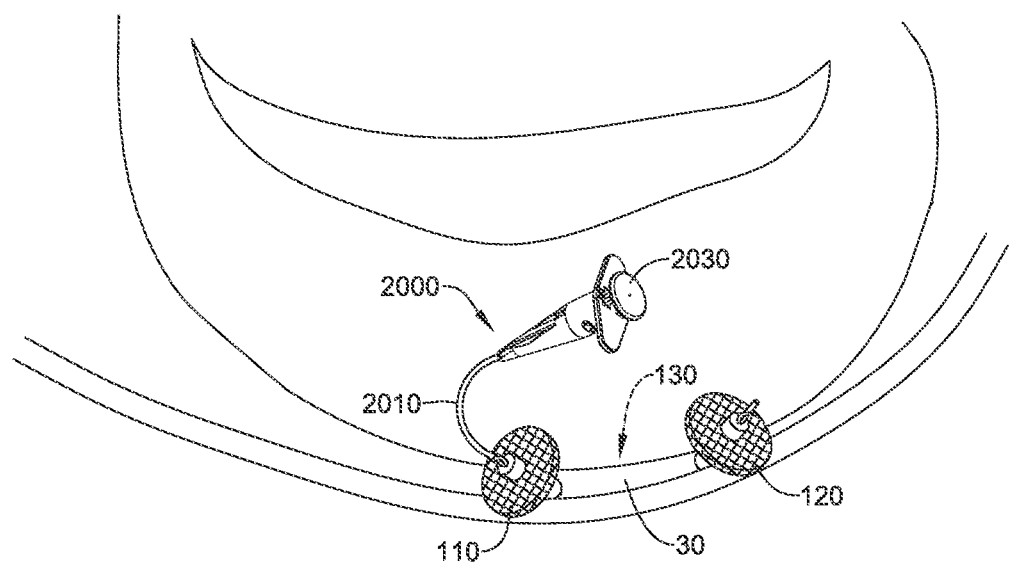
Figure 41:
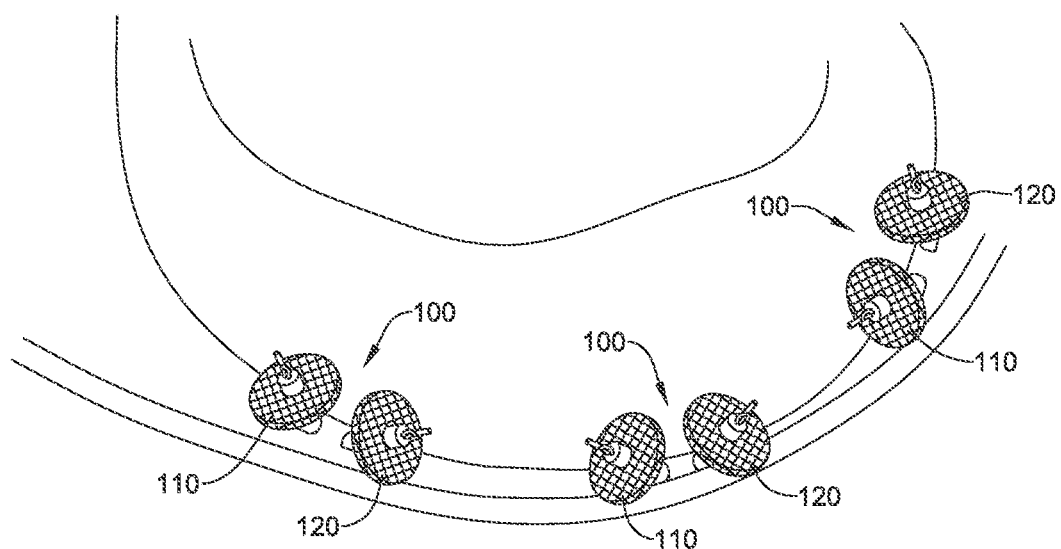

FIGS. 38-41 illustrate an example method of deploying a body 100 of a heart valve anchor apparatus using the tissue penetrating device(s) and/or the delivery tool(s) 2000 of FIGS. 34-37. As seen in FIG. 38, a tissue penetrating device such as a delivery tool 2000 (the handle 2300 of FIG. 36 is shown for illustration, but any of the delivery tools 2000 may be used) may be directed into tissue 30 of a heart valve annulus (e.g., an annulus of the tricuspid valve 12, the pulmonary valve 14, the aortic valve 16, or the mitral valve 18). It is to be noted that while a bicuspid heart valve having two valve leaflets (e.g., the mitral valve 18, etc.) is illustrated in the figures, the same method may be applied to a heart valve having three valve leaflets (e.g., the pulmonary valve 14, the tricuspid valve 12, the aortic valve 16, etc.). The method may also be applied from either the upstream side or the downstream side of the heart valve, depending upon the approach used (e.g., surgical, intravascular, subclavian, aortic, femoral, arterial, venous, etc.). The tissue penetrating device, for example the delivery tool 2000 and/or the needle 2010, may be directed into the tissue 30 from a first side of the heart valve annulus, through the tissue 30, and back out the first side of the heart valve annulus, as seen in FIG. 38. Additional details related to the passage and/or path of the heart valve anchor apparatus through the tissue 30 have been discussed previously with respect to FIGS. 29-31. After the needle 2010 has passed through the tissue 30, the actuator element 2030 and/or the push rod disposed within the delivery tool 2000 may be axially translated distally to begin releasing the body 100 out of the needle 2010. While the needle 2010 is positioned with its distal end protruding from (e.g., the first side or the second side of the heart valve annulus, depending on the method and/or approach used) the tissue 30, the second radially expandable portion 120 may be pushed out of the needle 2010, where it expands to the expanded or unstressed configuration, as seen in FIG. 39 for example. The needle 2010 and/or the handle of the delivery tool 2000 may be pulled proximally back through from the tissue 30 as discussed above until the second radially expandable portion 120 engages the tissue 30. Further proximal translation of the delivery tool 2000 and/or the needle 2010 may be combined with additional axial translation of the actuator element 2030, and/or the push rod, to release the root portion 130 of the body 100 from the delivery tool 2000 and/or the needle 2010 within the tissue 30. From this point, the delivery tool 2000 and/or the needle 2010 is pulled away from (e.g., translated proximally relative to) the second radially expandable portion 120, thereby releasing the first radially expandable portion 110 outside of the tissue 30, as seen in FIG. 40, such that the first radially expandable portion 110 and the second radially expandable portion 120 both engage the tissue 30 disposed between them in the unstressed configuration. In some embodiments, the suture element 1200 (if present) may be severed, broken, or cut to release the body 100. In some embodiments, the body 100 may be transitioned from the expanded or unstressed configuration toward and/or to the shortened configuration, as shown in FIG. 41 for example, in one of the methods or steps described above. In the shortened configuration, the tissue 30 may be compressed between the first radially expandable portion 110 and the second radially expandable portion 120.

In any given method or application of the heart valve anchor apparatus, at least one heart valve anchor apparatus may be deployed within a heart valve annulus. In some example, the at least one heart valve anchor apparatus may include two, three, four, or more heart valve anchor apparatus deployed within the heart valve annulus as necessary to sufficiently reduce, tighten, and/or contract the heart valve annulus to bring the free edges of the heart valve leaflets back into apposition when the heart valve is closed. In some embodiments, at least one heart valve anchor apparatus may be deployed within or adjacent the annulus of one, more than one, or each cusp or leaflet of the heart valve being treated. It has been found that the body of the heart valve anchor apparatus may sufficiently influence the tissue of the heart valve annulus to resolve heart valve regurgitation in the expanded or unstressed configuration, or the body of the heart valve anchor apparatus may be transitioned to the shortened configuration when additional influence is needed to resolve heart valve regurgitation.

In some embodiments, a seal member may be circumferentially disposed on and/or about a portion of the body 100, and as the term suggests, may help to seal an exterior of the body 100 within and/or against the tissue 30 upon deployment (e.g., in the expanded, unstressed, and/or shortened configurations), thereby preventing leakage around the body 100. In some embodiments, the seal member may be disposed about, on, and/or radially outward of an outside surface of the body 100, including one or more of the first radially expandable portion 110, the second radially expandable portion 120, and/or the root portion 130. Additionally, the lumen extending through the body 100 may include a seal member disposed in the lumen and/or at the proximal and/or distal ends of the lumen, to prevent leakage through the body 100. In some embodiments, the seal member(s) may be formed from a polymeric material or other suitable biocompatible material. In some embodiments, the seal member(s) may be added or applied to the body 100 using one or more suitable techniques, such as but not limited to, mechanical attachment, adhesives, coating, electro-spinning, etc. In some embodiments, the seal member(s) may be configured to fold, pleat, compress, expand outward, or otherwise change shape as the body 100 changes configuration.

The materials that can be used for the various components of the body 100-900, the tissue penetrating device, the elongated sheath 1300, the delivery tool(s) 2000, etc. (and/or other systems disclosed herein) and the various elements thereof disclosed herein may include those commonly associated with medical devices. For simplicity purposes, the following discussion makes reference to the body 100-900, the tissue penetrating device, the elongated sheath 1300, the delivery tool(s) 2000, etc. However, this is not intended to limit the devices and methods described herein, as the discussion may be applied to other elements, members, components, or devices disclosed herein, such as, but not limited to, the body 100-900, the tissue penetrating device, the elongated sheath 1300, the delivery tool(s) 2000, etc. and/or elements or components thereof.

In some embodiments, the body 100-900, the tissue penetrating device, the elongated sheath 1300, the delivery tool(s) 2000, etc., and/or components thereof (such as, but not limited to, the deployment head 1310, the needle 1100, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the body 100-900, the tissue penetrating device, the elongated sheath 1300, the delivery tool(s) 2000, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the body 100-900, the tissue penetrating device, the elongated sheath 1300, the delivery tool(s) 2000, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the body 100-900, the tissue penetrating device, the elongated sheath 1300, the delivery tool(s) 2000, etc. to achieve the same result.

In some embodiments, a degree of Magnetic Resonance Imaging (MRI) compatibility is imparted into the body 100-900, the tissue penetrating device, the elongated sheath 1300, the delivery tool(s) 2000, etc. For example, the body 100-900, the tissue penetrating device, the elongated sheath 1300, the delivery tool(s) 2000, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The body 100-900, the tissue penetrating device, the elongated sheath 1300, the delivery tool(s) 2000, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the body 100-900, the tissue penetrating device, the elongated sheath 1300, the delivery tool(s) 2000, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the body 100-900 may include a fabric material disposed over or within the stent structure and/or the plurality of wires. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A method of deploying a heart valve anchor apparatus, comprising:
   inserting a tissue penetrating device into tissue forming a heart valve annulus such that a distal end of the tissue penetrating device protrudes from the tissue, the tissue penetrating device having a heart valve anchor apparatus disposed within a lumen of the tissue penetrating device in a delivery configuration, the heart valve anchor apparatus comprising:
      a body comprising:
         a first radially expandable portion at a proximal portion of the body;
         a second radially expandable portion at a distal portion of the body; and
         a root portion extending from the first radially expandable portion to the second radially expandable portion, the root portion having an outer extent;
      wherein the first radially expandable portion is configured to self-expand to an outer extent greater than the outer extent of the root portion when radially unconstrained;
      wherein the second radially expandable portion is configured to self-expand to an outer extent greater than the outer extent of the root portion when radially unconstrained;
   actuating a handle element of the tissue penetrating device to push the second radially expandable portion out of the distal end of the tissue penetrating device outside of the tissue;
   withdrawing the tissue penetrating device through the tissue, thereby releasing the root portion within the tissue and the first radially expandable portion outside of the tissue, such that the first radially expandable portion and the second radially expandable portion both engage the tissue disposed between them in an unstressed configuration;
   wherein in the unstressed configuration, the body defines a longitudinal centerline that extends away from a plane tangent to the root portion.

2. The method of claim 1, wherein the heart valve anchor apparatus further includes a suture element extending longitudinally through the body to a stop feature disposed distally of the second radially expandable portion, and the method further includes the step of:
   applying tension to a proximal portion of the suture element while applying a distally-directed force to the proximal portion of the body to place the body into a shortened configuration wherein the tissue is compressed between the first radially expandable portion and the second radially expandable portion.

* * * * *